(12) United States Patent
Biato et al.

(10) Patent No.: US 10,912,727 B2
(45) Date of Patent: *Feb. 9, 2021

(54) COMPOSITION AND PROCESS FOR TREATING HAIR

(71) Applicant: L'OREAL, Paris (FR)

(72) Inventors: Camila Maciel Biato, Rio de Janeiro (BR); Erika Alegrio Jarque Petali, Rio de Janeiro (BR); Bruno Maiko Sato, Rio de Janeiro (BR); Sintia Aguiar, Rio de Janeiro (BR); Serge Restle, Rio de Janeiro (BR); Liliane De Almeida Silvestre, Rio de Janeiro (BR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/563,182

(22) PCT Filed: Apr. 1, 2016

(86) PCT No.: PCT/BR2016/050074
§ 371 (c)(1),
(2) Date: Sep. 29, 2017

(87) PCT Pub. No.: WO2016/154701
PCT Pub. Date: Oct. 6, 2016

(65) Prior Publication Data
US 2018/0078474 A1    Mar. 22, 2018

(30) Foreign Application Priority Data

Apr. 2, 2015  (WO) ................ PCT/BR2015/050037
Dec. 23, 2015 (WO) ................ PCT/BR2015/050270

(51) Int. Cl.
*A61K 8/46* (2006.01)
*A61Q 5/04* (2006.01)
*A61K 8/73* (2006.01)
*A45D 7/06* (2006.01)
*A61K 8/19* (2006.01)
(Continued)

(52) U.S. Cl.
CPC .................. *A61K 8/46* (2013.01); *A45D 7/06* (2013.01); *A61K 8/19* (2013.01); *A61K 8/31* (2013.01);
(Continued)

(58) Field of Classification Search
None
See application file for complete search history.

(56) References Cited

U.S. PATENT DOCUMENTS 4,240,450 A     12/1980 Grollier et al.
2008/0025938 A1*  1/2008 Cassier .................. A61K 8/447
                                                          424/70.5
(Continued)

FOREIGN PATENT DOCUMENTS

EP    2332515 A1    6/2011
JP    2007176898 A * 7/2007

OTHER PUBLICATIONS

Ngus Chemical Company "AMP-Ultra PC Specialty Neutralizers" <http://latinamerica.in-cosmetics.com/_novadocuments/255482=636054135038200000> available May 2015; accessed Sep. 14, 2018 (Year: 2015).*

(Continued)

*Primary Examiner* — Nicole P Babson
(74) *Attorney, Agent, or Firm* — Polsinelli PC

(57) ABSTRACT

Disclosed herein is hair cosmetic composition comprising a thiol-based compound selected from thiolactic acid and its derivatives or salts, and wherein the composition has a pH of less than 7. Also disclosed is a process for shaping or altering the shape of hair or caring of the hair.

21 Claims, 1 Drawing Sheet

(51) Int. Cl.
*A61K 8/31* (2006.01)
*A61K 8/34* (2006.01)
*A61K 8/41* (2006.01)
*A61K 8/58* (2006.01)
*A61K 8/81* (2006.01)
*A61K 8/891* (2006.01)
*A61K 8/892* (2006.01)
*A61K 8/898* (2006.01)
*A61K 8/894* (2006.01)

(52) U.S. Cl.
CPC ............... *A61K 8/342* (2013.01); *A61K 8/41* (2013.01); *A61K 8/58* (2013.01); *A61K 8/585* (2013.01); *A61K 8/731* (2013.01); *A61K 8/817* (2013.01); *A61K 8/891* (2013.01); *A61K 8/892* (2013.01); *A61K 8/894* (2013.01); *A61K 8/898* (2013.01); *A61Q 5/04* (2013.01); *A61K 2800/48* (2013.01)

(56) References Cited

U.S. PATENT DOCUMENTS

2012/0183483 A1* 7/2012 Misu .................. A61K 8/19
424/70.2
2014/0261518 A1* 9/2014 Savaides .................. A61K 8/65
132/206

OTHER PUBLICATIONS

English translation of JP-2007176898-A (Year: 2007).*
Ingredients <https://www.ingredientstodiefor.com/item/HydroxyEthylCellulose_HEC_/1333/> available Jul. 30, 2013; accessed Apr. 30, 2020), (Year: 2013).*
International Search Report and Written Opinion dated Sep. 22, 2016 issued in corresponding International Application No. PCT/BR2016/050074, 8 Pages.

* cited by examiner

ASSESSMENTS OF STRAIGHTENING PERFORMANCE AND REDUCTION OF FRIZZINESS AND VOLUME OF HAIR
| BEFORE TREATMENT | RINSE PROTOCOL | NON-RINSE PROTOCOL |
|---|---|---|
|  | 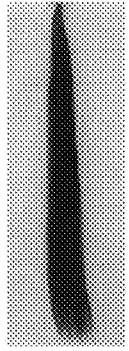 | 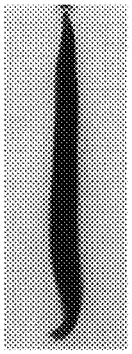 |
| Measurable attribute value: | 4.0 | 3.0 |

COMPOSITION AND PROCESS FOR TREATING HAIR

RELATED APPLICATIONS

This application is a national stage application (under 35 U.S.C. § 371) of PCT/BR2016/050074, filed Apr. 1, 2016, which claims benefit of PCT/BR2015/050270, filed on Dec. 23, 2015, and PCT/BR2015/050037, filed Apr. 2, 2015, all of which are incorporated herein by reference in their entirety.

FIELD OF THE INVENTION

The present application relates to a composition and a process involving applying the composition onto hair, wherein the composition contains an thiol-based compound selected from thiolactic acid and its derivatives or its salts, and wherein the composition has a pH of less than 7.

BACKGROUND OF THE INVENTION

Cosmetic and personal care products for use on keratinous substrates such as hair are available commercially in various forms, for example, as creams, lotions, gels, pastes, and powders. Regardless of the form, these products have to achieve and provide certain benefits and attributes such as efficaciousness, cosmeticity, desirable texture, stable formulations, and ease and convenience of use and application. Thus, in order to meet changing consumer needs and preferences, manufacturers of such products continuously seek to re-formulate and create new products with enhanced efficacy, while still remaining stable and safe to use. In addition, manufacturers continue to test the use of new raw materials and ingredients or new product forms that would help deliver the desired attributes and properties with respect to viscosity, texture, stability and efficacy.

One area where manufacturers are always seeking to improve in is in the area of hair cosmetic products such as those products designed to change the appearance, shape or configuration of hair as well as to provide hair care benefits of manageability, frizz control, volume reduction, and improved quality of the hair fiber. Examples of such hair cosmetic products are hair relaxers or hair straighteners which can relax or straighten curly or kinky hair, including wavy hair. Other hair cosmetic products are perms and waving compositions for providing curl or shape to hair. These products may increase the manageability and ease of styling hair and they may either be applied in a hair salon by a professional or in the home by the individual consumer.

One type of composition that can be applied onto hair in order to change its shape and make it more manageable is an alkaline composition. Alkaline hair relaxing/straightening involves hydrolyzing the keratin of the hair with various alkaline agents, such as inorganic hydroxides, for instance sodium hydroxide, or organic hydroxides, such as guanidine hydroxide, or organic amines. Hair relaxing/straightening products that employ sodium hydroxide or potassium hydroxide are also called lye-based products and products that use other alkaline agents such as lithium hydroxide, calcium hydroxide, organic hydroxides and other non-hydroxide compounds, for example, organic amines, generally fall under the category of no-lye products.

Still, it is desirable to find alternatives to the alkaline lye- and no-lye-based products and process described above which can damage the hair by weakening and/or causing dryness of the hair fibers. However, the discovery of new compositions and processes for changing the shape of hair that impart less or minimal damage to hair, may pose challenges to manufacturers and formulators because the incorporation of new ingredients into the compositions may negatively impacting their performance, cosmetic attributes, and formulation stability. In addition, the alkalinity and/or pH is an important consideration for these products. New processes of treating and changing the shape of hair may also impact the performance of the compositions, processing times and quality of use.

The present invention provides a hair cosmetic composition for shaping or altering the shape of hair or caring of the hair, the composition containing an thiol-based compound selected from thiolactic acid, thiolactic acid derivatives, their salts, and mixtures thereof, optionally a neutralizing agent, and water, wherein the composition is non-alkaline such that its pH ranges from about 2 to less than about 7. The present invention also provides a process for shaping or altering the shape of hair or caring of the hair, such as by straightening the hair or by providing improved manageability to the hair, in an easy and efficacious manner, the process comprising applying onto the hair, said composition and heating the hair while optionally applying a smoothing action on the hair, and optionally, rinsing the hair with water or contacting the hair with an intermediate agent selected from a shampoo and/or a conditioner, followed by rinsing with water. The treatment of hair in accordance with the process of the present disclosure can be followed by a step of contacting the hair with a neutralizing composition containing an oxidizing agent. Such neutralizing composition can be a rinse-off or leave-in product. The hair can also be contacted with a pre-treatment composition such as a shampoo, then rinsed with water before the hair cosmetic composition is applied onto the hair or other pre-treatment compositions which may be leave-in or rinse-off compositions.

It was surprisingly and unexpectedly discovered that the composition of the present invention, when applied onto hair fibers, result in an effective process of shaping or altering the shape of hair or providing hair care benefits to hair such as manageability, frizz control and volume reduction. In addition, the process of the invention allows the straightening or texlaxing (results in wavy hair) of hair while at the same time, limiting or avoiding the degradation of hair resulting from alkaline systems and maintaining desirable working conditions, especially since there is no excessive vaporization of the composition at the time of treating the hair in accordance with the hair treatment process according to the invention. The hair treatment process according to the invention also makes it possible to minimize the problems of breakage of the hair fibers. The composition and the process of the invention were also found to improve the physical properties and appearance of hair, by durably reducing or controlling the volume and frizziness of hair.

BRIEF SUMMARY OF THE INVENTION

The present invention relates to a hair cosmetic composition comprising:
(a) at least one thiol-based compound selected from thiolactic acid, thiolactic acid derivatives, their salts, and mixtures thereof;
(b) optionally, at least one neutralizing agent; and
(c) water;
wherein the pH of the composition ranges from about 2 to less than about 7.

The present invention also relates to a process for shaping hair or altering the shape of hair, the process comprising the steps of:
(1) applying onto hair, the above-described composition:
(2) optionally, brushing or combing or smoothing the hair;
(3) heating the hair at a temperature of at least 40° C.; while optionally applying a smoothing action on the hair; and
(4) optionally, rinsing the hair with water.

The hair can be contacted after step (3) with an intermediate agent selected from a shampoo and/or a conditioner, followed by rinsing with water.

The hair can also be contacted with a shampoo or a conditioner, then rinsed with water before the hair cosmetic composition is applied onto the hair.

The hair can also be contacted with a pre-treatment composition before the hair cosmetic composition is applied onto the hair.

Methods of making the compositions of the present invention are also disclosed in this disclosure.

According to the present invention, the composition of the invention is preferably in the form of an emulsion, for example, oil-in-water emulsion and water-in-oil emulsion or in the form of a gel or lotion or aqueous solution.

It is to be understood that both the foregoing general description and the following detailed description are exemplary and explanatory only, and are not restrictive of the invention.

BRIEF DESCRIPTION OF THE DRAWING

The FIG. provides photographic images of hair samples, showing the straightening/shaping effects on hair after being contacted with the hair cosmetic composition and treated according to the processes of the present disclosure.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−10% of the indicated number (e.g. "about 10%" means 9%-11% and "about 2%" means 1.8%-2.2%), such as within 9%, 8%, 7%, 6%, 5%, 4%, 3%, 2%, or 1%, according to various embodiments.

"Keratinous substrates" as used herein, includes, but is not limited to keratin fibers such as hair on the human head and hair comprising eyelashes. "Keratinous substrates" as used herein, may also refer to the skin such as lips, finger nails or toe nails, and the scalp.

As used herein, the terms "applying a composition onto "keratinous substrates" as used herein, includes, and "applying a composition onto "keratinous substrates" or "keratin fibers" such as hair on a human head with at least one of the compositions of the disclosure, in any manner.

The term "treat" (and its grammatical variations) as used herein refers to the application of the compositions of the present disclosure onto the surface of keratinous substrates such as hair. The term 'treat' (and its grammatical variations) as used herein also refers to contacting keratinous substrates such as hair with the compositions of the present disclosure.

The term "rinse-off" is used herein to mean that a keratinous substrate such as hair is rinsed and/or washed with water either after or during the application of a composition onto the keratinous substrate, and before drying and/or shaping said keratinous substrate. At least a portion of the composition is removed from the keratinous substrate during the rinsing and/or washing. A "rinse-off" product refers to a composition such as a hair care composition that is rinsed and/or washed with water either after or during the application of the composition onto the keratinous substrate, and before drying and/or styling said keratinous substrate.

A "leave-on" product refers to a cosmetic composition such as a hair cosmetic composition that is applied to a keratinous substrate such as hair and not further subjected to a rinsing and/or washing step before drying and/or shaping the substrate.

The term "stable" as used herein means that the composition does not exhibit phase separation and/or crystallization.

"Volatile", as used herein, means having a flash point of less than about 100° C.

"Non-volatile", as used herein, means having a flash point of greater than about 100° C.

"Reducing agent" as used herein, means an agent capable of reducing the disulfide bonds of the hair.

"Active material" as used herein with respect to the percent amount of an ingredient or raw material, refers to 100% activity of the ingredient or raw material.

The compositions and processes of the present invention can comprise, consist of, or consist essentially of the essential elements and limitations of the invention described herein, as well as any additional or optional ingredients, components, or limitations described herein or otherwise useful.

In one embodiment, the present invention relates to a hair cosmetic composition comprising:
(a) at least one thiol-based compound selected from thiolactic acid, thiolactic acid derivatives, their salts and mixtures thereof, and present in an amount of from about 1% to about 15% by weight, preferably from about 1.5% to about 12% by weight, more preferably from about 2% to about 10% by weight, even more preferably from about 3% to about 9% by weight;
(b) optionally, at least one neutralizing agent selected from organic amines, alkali metal hydroxides, alkali earth metal hydroxides, alkali metal carbonates, alkali metal phosphates, and mixtures thereof, preferably from aminomethyl propanol, sodium hydroxide, potassium hydroxide, lithium hydroxide, aminomethyl propanediol, triisopropanol amine, dimethylstearylamine, dimethyl/tallowamine, lysine, ornithine, arginine, monoethanolamine, triethanolamine, calcium hydroxide, calcium bicarbonate, and mixtures thereof; and
(c) water;
all weights being based on the total weight of the composition;
wherein the pH of the composition ranges from about 2 to less than about 7;
wherein when the at least one neutralizing agent is selected from aminomethyl propanol, the aminomethyl propanol is present in an amount of from about 0.1% to about 6.3% by weight;
wherein when the at least one neutralizing agent is selected from sodium hydroxide, the sodium hydroxide is present in an amount of from about 0.1% to about 4.1% by weight; and wherein when the at least one neutralizing agent is selected from monoethanolamine, the monoethanolamine is present in an amount of from about 0.1% to about 4.1% by weight.

In another embodiment, the present invention relates a hair cosmetic composition comprising:
  (a) from about 1.5% to about 12% by weight of at least one thiol-based compound selected from thiolactic acid;
  (b) optionally, at least one neutralizing agent;
  (c) at least one fatty substance;
  (d) at least one quaternary ammonium compound; and
  (e) water;
  all weights being based on the total weight of the composition;
  wherein the pH of the composition ranges from about 2 to about 6.5.

In yet another embodiment, the present invention relates to a hair cosmetic composition comprising:
  (a) from about 2% to about 10% by weight of at least one thiol-based compound selected from thiolactic acid;
  (b) at least one neutralizing agent;
  (c) at least one fatty substance selected from from alkanes, esters of fatty acid, esters of fatty alcohol, hydrocarbons, silicones, non-silicone waxes, mineral oil, vegetable oils, non-silicone synthetic oils, fatty alcohols and mixtures thereof, preferably mineral oil, stearyl alcohol, cetearyl alcohol, cetyl alcohol, and mixtures thereof;
  (d) at least one quaternary ammonium compound selected from behentrimoinium chloride, cetrimonium chloride, behentrimonium methosulfate, quaternium-87, quaternium-83, and polyquaternium compounds such as polyquaternium-6, or polyquaternium 10, or polyquaternium-67, and mixtures thereof; and
  (e) water;
  all weights being based on the total weight of the composition;
  wherein the pH of the composition ranges from about 2 to about 5.

In another embodiment, the present invention relates to a hair cosmetic composition comprising:
  (a) from about 3% to about 9% by weight of at least one thiol-based compound selected from thiolactic acid;
  (b) at least one neutralizing agent;
  (c) from about 1% to about 80% by weight at least one fatty substance comprising oils and fatty alcohols;
  (d) from about 0.1% to about 20% by weight of at least one nonionic surfactant selected from alkoxylated fatty alcohols, alkyl(ether)phosphates, alkylpolyglucosides, and mixtures thereof, preferably from alkyl(ether)phosphates such as PPG-5-Ceteth-10 phosphate, Oleth-3 phosphate, Oleth-10 phosphate, Ceteth-10 phosphate, a mixture of Ceteth-10 phosphate and Dicetyl phosphate, Dicetyl phosphate, Cetyl phosphate, or Stearyl phosphate; and
  (e) water;
  all weights being based on the total weight of the composition;
  wherein the pH of the composition ranges from about 2 to about 5.

In yet another embodiment, the present invention relates to a hair cosmetic composition comprising:
  (a) from about 3% to about 9% by weight of at least one thiol-based compound selected from thiolactic acid;
  (b) at least one neutralizing agent;
  (c) from about 1% to about 80% by weight at least one fatty substance comprising oils and fatty alcohols;
  (d) from about 0.1% to about 20% by weight of at least one nonionic surfactant selected from alkoxylated fatty alcohols, alkyl(ether)phosphates, alkylpolyglucosides, and mixtures thereof, preferably from alkyl(ether)phosphates such as PPG-5-Ceteth-10 phosphate, Oleth-3 phosphate, Oleth-10 phosphate, Ceteth-10 phosphate, a mixture of Ceteth-10 phosphate and Dicetyl phosphate, Dicetyl phosphate, Cetyl phosphate, or Stearyl phosphate;
  (e) at least one quaternary ammonium compound selected from behentrimoinium chloride, cetrimonium chloride, behentrimonium methosulfate, quaternium-87, quaternium-83, and polyquaternium compounds such as polyquaternium-6, or polyquaternium 10, or polyquaternium-67, and mixtures thereof; and
  (f) water;
  all weights being based on the total weight of the composition;
  wherein the pH of the composition ranges from about 2 to about 5.

In certain embodiments, the above-described compositions of the present disclosure comprises at least two fatty substances selected from oils such as mineral oil and fatty alcohols such as stearyl alcohol, cetearyl alcohol, cetyl alcohol, and mixtures thereof.

In other embodiments, the above-described compositions of the present disclosure comprises at least two nonionic surfactants selected from PPG-5-Ceteth-10 phosphate, Oleth-3 phosphate, Oleth-10 phosphate, Ceteth-10 phosphate, a mixture of Ceteth-10 phosphate and Dicetyl phosphate, Dicetyl phosphate, Cetyl phosphate, Stearyl phosphate, and mixtures thereof.

In yet another embodiment, the present invention relates to a hair cosmetic composition comprising:
  (a) from about 3% to about 9% by weight of at least one thiol-based compound selected from thiolactic acid;
  (b) at least one neutralizing agent;
  (c) from about 0.5% to about 8% by weight of at least one silicone compound;
  (d) from about 0.3% to about 1.5% by weight of at least one thickening agent selected from thickening polymers comprising at least one sugar unit, for instance nonionic guar gums, optionally modified with C1-C6 hydroxyalkyl groups, biopolysaccharide gums of microbial origin, such as scleroglucan gum or xanthan gum, gums derived from plant exudates, such as gum arabic, ghatti gum, karaya gum, gum tragacanth, carrageenan gum, agar gum and carob gum, pectins, alginates, starches, hydroxy(C1-C6)alkylcelluloses (hydroxyalkyl celluloses), and carboxy(C1-C6)alkylcelluloses, and mixtures thereof, preferably, hydroxyalkyl celluloses; and
  (e) water;
  all weights being based on the total weight of the composition;
  wherein the pH of the composition ranges from about 2 to less than about 7.

In an embodiment, the present invention relates to a process for straightening hair, the process comprising the steps of:
  (1) optionally, contacting hair with a shampoo and/or conditioner, followed by rinsing the hair with water;
  (2) applying onto the hair, any one of the above-described compositions of the present disclosure,
  (3) optionally, brushing or combing or smoothing the hair;
  (4) heating the hair at a temperature of at least 40° C.; while optionally applying a smoothing action on the hair; and (5) optionally, rinsing the hair with water or contacting the hair with an intermediate agent selected from a shampoo and/or a conditioner, followed by rinsing with water; and (6) optionally, contacting the hair with a neutralizing composition comprising an oxidizing agent.

Preferably, the above-described process comprises the steps of:

(1) first, applying onto the hair, any one of the above-described compositions of the invention;

(2) second, brushing or combing or smoothing the hair;

(3) third, heating the hair at a temperature of at least 40° C.; while optionally applying a smoothing action on the hair; and (4) fourth, heating the hair at a temperature of at least 40° C.; while optionally applying a smoothing action on the hair.

In certain embodiments, the heating step in any one of the above-described processes of the invention is preferably accomplished by use of device such as a blow dryer, a flat iron, a hair dryer, a heat lamp, a heat wand, a heating hood, a heating cap, a heating rod, heating curlers/rods or steam curlers. When a hair dryer or blow dryer is used, a brush or comb or the fingers may be passed one or more times over or through the hair.

The heating step in any one of the above-described processes of the invention may also be accompanied by a smoothing action on the hair, preferably performed with a mechanical or physical device, for example, the plates of a flat iron or a hair brush.

In certain embodiments, the heating step in any one of the above-described processes is accomplished at a temperature higher than 100° C.

In other embodiments, the heating step in any one of the above-described processes is accomplished at a temperature of up to 100° C.

In yet other embodiments, the heating step in any one of the above-described processes is accomplished at a temperature of higher than 50° C.

In certain embodiments, the above-described compositions employed in any one of the above-described processes of the invention is allowed to remain on the hair for a predetermined amount of time sufficient to shape or alter the shape or provide hair benefits to hair (e.g., manageability, frizz control or volume reduction).

In preferred embodiments, the composition in any one of the above-described processes of the invention is a hair straightening composition. In yet other preferred embodiments, said hair straightening composition is allowed to remain on the hair for a predetermined amount of time sufficient as to achieve a desired degree of hair straightening.

In yet other preferred embodiments, the composition in any one of the above-described processes of the invention is a hair care composition.

In yet other preferred embodiments, the composition in any one of the above-described processes of the invention is a hair styling composition.

It was surprisingly and unexpectedly discovered that the application of the compositions of the present invention when used in combination with the process of the present invention, resulted in effectively shaped or styled or straightened hair.

It was also surprisingly and unexpectedly discovered that when the composition of the invention additionally contained one or more of nonionic surfactants, fatty substances, quaternary ammonium compounds, thickening agents, and silicone compounds, the composition had a smooth, non-drip, and homogenous texture/consistency. The non-drip consistency of the compositions of the present invention is desirable because it helps the compositions to remain on the hair for a predetermined amount of time as to achieve the desired cosmetic effects.

Thiol-Based Compounds

The present invention employs at least one thiol-based compound selected from thiolactic acid, thiolactic acid derivatives, their salts, and mixtures thereof.

The at least one thiol-based compound of the present disclosure can be used in combination with other thiol-based compounds selected from thioglycolic acid, cysteine, cysteamine, homocystine, glutathione, thioglycerol, thiomalic acid, 2-mercaptopropionic acid, 3-mercaptopropionic acid, thio diglyco I, 2-mercaptoethanol, dithiothreitol, thioxanthine, thiosalicylic acid, thiopropionic acid, lipoic acid, N-acetylcysteine, their salts thereof, and mixtures thereof.

The at least one thiol-based compound of the present disclosure can be also be used in combination with non-thiol based compounds such as alkali metal, alkaline-earth metal sulfites, hydrides or phosphines, and mixtures thereof.

In certain embodiments, the thiol-based compound used in the composition of the invention is thiolactic acid.

The at least one thiol-based compound can be employed in the compositions of the present invention in an amount of from about 1% to about 15% by weight, preferably from about 1.5% to about 10% by weight, more preferably from about 2% to about 8% by weight, more preferably from about 3% to about 9% by weight, based on the total weight of the composition, including all ranges and subranges therebetween.

In certain embodiments, the at least one thiol-based compound is selected from thiolactic acid and is employed in the composition of the present invention in an amount of about 1%, 1.25%, 1.5%, 1.75%, 2%, 2.25%, 2.5%, or about 2.75%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.5%, 10%, 10.5%, 11%, 11.5%, 12%, 13%, or 14%, by weight, based on the total weight of the composition.

Neutralizing Agent

Suitable neutralizing agents may be selected from alkali metal carbonates, alkali metal phosphates, organic amines, hydroxide base compounds, and mixtures thereof, particularly from organic amines, alkali metal hydroxides, alkali earth metal hydroxides, and mixtures thereof.

Organic amines may be selected from amino-2-methyl-1-propanol (or aminomethyl propanol), ethylamines, ethyleneamines, alkanolamines, cyclic amines and other cyclic compounds, saturated or unsaturated, having one or more nitrogen atoms within the ring, and mixtures thereof.

The organic amines may be chosen from the ones having a pKb at 25° C. of less than 12, such as less than 10 or such as less than 6. It should be noted that this is the pKb corresponding to the function of highest basicity.

Organic amines may be chosen from organic amines comprising one or two primary, secondary, or tertiary amine functions, and at least one linear or branched C1-C8 alkyl groups bearing at least one hydroxyl radical.

Organic amines may also be chosen from alkanolamines such as mono-, di- or trialkanolamines, comprising one to three identical or different C1-C4 hydroxyalkyl radicals, ethylamines, ethyleneamines, quinoline, aniline and cyclic amines, such as pyrroline, pyrrole, pyrrolidine, imidazole, imidazolidine, imidazolidinine, morpholine, pyridine, piperidine, pyrimidine, piperazine, triazine and derivatives thereof.

Among the compounds of the alkanolamine type that may be mentioned include but not limited to: monoethanolamine (also known as monoethanolamine or MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, 2-amino-2-methyl-1-propanol, and tris(hydroxymethylamino)methane.

Other examples include but are not limited to: 1,3-diaminopropane, 1,3-diamino-2-propanol, spermine, and spermidine.

In some embodiments, the organic amines are chosen from amino acids.

As non-limiting examples, the amino acids that may be used may be of natural or synthetic origin, in L, D, or racemic form, and comprise at least one acid function chosen from, for instance, carboxylic acid, sulfonic acid, phosphonic acid, and phosphoric acid functions. The amino acids may be in their neutral or ionic form.

Amino acids that may be used in the present disclosure include but are not limited to: aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine, and valine.

Further as non-limiting examples, the amino acids may be chosen from basic amino acids comprising an additional amine function optionally included in a ring or in a ureido function. Such basic amino acids may be chosen from histidine, lysine, arginine, ornithine, and citrulline.

In some embodiments, the organic amines are chosen from organic amines of heterocyclic type. Besides histidine that has already been mentioned in the amino acids, non-limiting mention may also be made of pyridine, piperidine, imidazole, 1,2,4-triazole, tetrazole, and benzimidazole.

In some embodiments, the organic amines are chosen from amino acid dipeptides. Amino acid dipeptides that may be used in the present disclosure include but not limited to: carnosine, anserine, and baleine.

In some embodiments, the organic amines are chosen from compounds comprising a guanidine function. Organic amines of this type that may be used in the present disclosure include, besides arginine that has already been mentioned as an amino acid, creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid.

The alkali metal phosphates and carbonates that may be used are, for example, sodium phosphate, potassium phosphate, sodium carbonate, sodium bicarbonate, potassium carbonate, potassium bicarbonate, and their derivatives.

The hydroxide base compounds chosen from alkali metal hydroxides, alkaline-earth metal hydroxides, transition metal hydroxides, quaternary ammonium hydroxides, organic hydroxides, and mixtures thereof. Suitable examples are ammonium hydroxide, sodium hydroxide, potassium hydroxide, lithium hydroxide, rubidium hydroxide, caesium hydroxide, francium hydroxide, beryllium hydroxide, magnesium hydroxide, calcium hydroxide, strontium hydroxide, barium hydroxide, molybdenum hydroxide, manganese hydroxide, zinc hydroxide, cobalt hydroxide, cadmium hydroxide, cerium hydroxide, lanthanum hydroxide, actinium hydroxide, thorium hydroxide, aluminium hydroxide, guanidinium hydroxide and mixtures thereof.

The at least one neutralizing agent may be chosen from at least one organic amine such as at least one alkanolamine. Particularly preferred alkanolamines are 2-amino-2-methyl-1-propanol (aminomethyl propanol), ethanolamine (also known as monoethanolamine or MEA), triethanolamine, and mixtures thereof. An even more particularly preferred alkanolamine is ethanolamine.

According to at least one embodiment, the at least one neutralizing agent is chosen from aminomethyl propanol, sodium hydroxide, potassium hydroxide, lithium hydroxide, aminomethyl propanediol, triisopropanol amine, dimethylstearylamine, dimethyl/tallowamine, lysine, ornithine, arginine, monoethanolamine, triethanolamine, calcium hydroxide, calcium bicarbonate, and mixtures thereof.

According to another preferred embodiment, the at least one neutralizing agent is chosen from aminomethyl propanol, sodium hydroxide, lithium hydroxide, calcium hydroxide, monoethanolamine, and mixtures thereof.

In one preferred embodiment, the at least one neutralizing agent is selected from aminomethyl propanol and is present in an amount of from about 0.1% to about 6.3% by weight, preferably from about 0.2% to about 5.5% by weight, more preferably from about 0.3% to about 5% by weight, even more preferably from about 0.3% to about 4.6% by weight, based on the total weight of the composition, including all ranges and subranges there between.

In certain embodiments, the at least one neutralizing agent selected from aminomethyl propanol is employed in the compositions of the present invention in an amount of about 0.1%, 0.3%, 0.4%, 0.5%, 0.6%, 0.7%, 0.8%, 0.9%, 1%, 1.3%, 1.4%, 1.5%, 1.75%, 2%, 2.3%, 2.4%, 2.5%, 2.75%, or 3%, 3.3%, 3.5%, 3.75%, 4%, 4.3%, 4.5%, 4.6%, by weight, based on the total weight of the composition.

In another preferred embodiment, the at least one neutralizing agent is selected from sodium hydroxide and is present in an amount of from about 0.1% to about 4.1% by weight, preferably from about 0.15% to about 3.5% by weight, more preferably from about 0.2% to about 3% by weight, even more preferably from about 1% to about 3% by weight, based on the total weight of the composition, including all ranges and subranges therebetween.

In certain embodiments, the at least one neutralizing agent selected from sodium hydroxide is employed in the compositions of the present invention in an amount of about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, about 2.3%, 2.4%, 2.5%, 2.6%, 2.7%, 2.8%, 2.9%, 3%, based on the total weight of the composition.

In yet another preferred embodiment, the at least one neutralizing agent is selected from monoethanolamine and is present in an amount of from about 0.1% to about 6.3% by weight, preferably from about 0.2% to about 5.5% by weight, more preferably from about 0.3% to about 5% by weight, even more preferably from about 0.3% to about 4.6% by weight, based on the total weight of the composition, including all ranges and subranges there between.

In certain embodiments, the at least one neutralizing agent selected from monoethanolamine is employed in the compositions of the present invention in an amount of about 0.1%, 0.3%, 0.4%, 0.5%, 0.6%, 0.7%, 0.8%, 0.9%, 1%, 1.3%, 1.4%, 1.5%, 1.75%, 2%, 2.3%, 2.4%, 2.5%, 2.75%, or 3%, 3.3%, 3.5%, 3.75%, 4%, 4.3%, 4.5%, 4.6%, by weight, based on the total weight of the composition.

Fatty Substances

The present invention employs at least one fatty substance.

The term "fatty substance" means an organic compound that is insoluble in water at ordinary room temperature (25 degrees centigrade) and at atmospheric pressure (760 mmHg) (solubility of less than 5 percent, preferably 1 percent and even more preferentially 0.1 percent). They have in their structure at least one hydrocarbon-based chain containing at least 6 carbon atoms or a sequence of at least two siloxane groups. In addition, the fatty substances are generally soluble in organic solvents under the same temperature and pressure conditions, for instance chloroform, ethanol, benzene, liquid petroleum jelly or decamethylcyclopentasiloxane.

The fatty substance may be selected from alkanes, esters of fatty acid, esters of fatty alcohol, hydrocarbons, non-silicone waxes, mineral oil, vegetable oils, non-silicone synthetic oils, fatty alcohols, and mixtures thereof.

The fatty substances are especially chosen from $C_6$-$C_{16}$ hydrocarbons, hydrocarbons containing more than 16 carbon atoms and in particular alkanes, oils of animal origin, oils of plant origin, glycerides or fluoro oils of synthetic origin, fatty acid and/or fatty alcohol esters, and non-silicone waxes.

It is recalled that, for the purposes of the invention, the fatty esters and fatty acids more particularly contain one or more linear or branched, saturated or unsaturated hydrocarbon-based groups comprising 6 to 30 carbon atoms, which are optionally substituted, in particular with one or more (in particular 1 to 4) hydroxyl groups. If they are unsaturated, these compounds may comprise one to three conjugated or unconjugated carbon-carbon double bonds.

As regards the $C_6$-$C_{16}$ alkanes, they are linear, branched or possibly cyclic. Mention may be made, by way of example, of hexane, dodecane or isoparaffins, such as isohexadecane or isodecane. The linear or branched hydrocarbons containing more than 16 carbon atoms may be chosen from liquid paraffins, petroleum jelly, liquid petroleum jelly, polydecenes, and hydrogenated polyisobutene such as Parleam®.

Among the animal oils, mention may be made of perhydrosqualene.

Among the triglycerides of plant or synthetic origin, mention may be made of liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, sunflower oil, castor oil, avocado oil, jojoba oil, shea butter oil and caprylic/capric acid triglycerides, for instance those sold by the company Stearineries Dubois or those sold under the names Miglyol® 810, 812 and 818 by the company Dynamit Nobel.

Among the fluoro oils, mention may be made of perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-(trifluoromethyl)perfluoromorpholine sold under the name PF 5052® by the company 3M.

The wax(es) that may be used in the anhydrous cosmetic composition (I) are chosen especially from carnauba wax, candelilla wax, esparto grass wax, paraffin wax, ozokerite, plant waxes, for instance olive wax, rice wax, hydrogenated jojoba wax or the absolute waxes of flowers such as the essential wax of blackcurrant blossom sold by the company Bertin (France), animal waxes, for instance beeswaxes, or modified beeswaxes (cerabellina); other waxes or waxy starting materials that may be used according to the invention are especially marine waxes such as the product sold by the company Sophim under the reference M82, and polyethylene waxes or polyolefin waxes in general.

As regards the esters of a fatty acid and/or of a fatty alcohol, which are advantageously different from the triglycerides mentioned above, mention may be made especially of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters more particularly being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates; 2-ethylhexyl palmitate; 2-octyldecyl palmitate; alkyl myristates, such as isopropyl, butyl, cetyl, 2-octyldodecyl, myristyl or stearyl myristate; hexyl stearate; butyl stearate; isobutyl stearate; dioctyl malate; hexyl laurate or 2-hexyldecyl laurate.

Still within the context of this alternative form, use may also be made of esters of $C_4$-$C_{22}$ di- or tricarboxylic acids and of $C_1$-$C_{22}$ alcohols and esters of mono-, di- or tricarboxylic acids and of di-, tri-, tetra- or pentahydroxy $C_2$-$C_{26}$ alcohols.

Mention may in particular be made of: diethyl sebacate; diisopropyl sebacate; diisopropyl adipate; di(n-propyl) adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, use is preferably made of ethyl, isopropyl, myristyl, cetyl or stearyl palmitate, 2-ethylhexyl palmitate, 2-octyldecyl palmitate, alkyl myristates, such as isopropyl, butyl, cetyl or 2-octyldodecyl myristate, hexyl stearate, butyl stearate, isobutyl stearate, dioctyl malate, hexyl laurate, 2-hexyldecyl laurate, isononyl isononanoate or cetyl octanoate.

The composition can also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars can be monosaccharides, oligosaccharides or polysaccharides.

Mention may be made, as suitable sugars, for example, of sucrose (or saccharose), glucose, galactose, ribose, fucose, maltose, fructose, mannose, arabinose, xylose, lactose and their derivatives, in particular alkyl derivatives, such as methyl derivatives, for example methylglucose.

The esters of sugars and of fatty acids can be chosen in particular from the group consisting of the esters or mixtures of esters of sugars described above and of saturated or unsaturated and linear or branched $C_6$-$C_{30}$ and preferably $C_{12}$-$C_{22}$ fatty acids. If they are unsaturated, these compounds can comprise from one to three conjugated or non-conjugated carbon-carbon double bonds.

The esters according to this alternative form can also be chosen from mono-, di-, tri- and tetraesters, polyesters and their mixtures.

These esters can, for example, be oleates, laurates, palmitates, myristates, behenates, cocoates, stearates, linoleates, linolenates, caprates, arachidonates or their mixtures, such as, in particular, oleate/palmitate, oleate/stearate or palmitate/stearate mixed esters.

More particularly, use is made of mono- and diesters and in particular mono- or di-oleate, -stearate, -behenate, -oleate/palmitate, -linoleate, -linolenate or -oleate/stearate of sucrose, glucose or methylglucose.

Mention may be made, by way of example, of the product sold under the name Glucate® DO by Amerchol, which is a methylglucose dioleate.

Mention may also be made, by way of examples of esters or mixtures of esters of sugar and of fatty acid, of:

the products sold under the names F160, F140, F110, F90, F70 and SL40 by Crodesta, respectively denoting sucrose palmitate/stearates formed of 73 percent monoester and 27 percent di- and triester, of 61 percent monoester and 39 percent di-, tri- and tetraester, of 52 percent monoester and 48 percent di-, tri- and tetraester, of 45 percent monoester and 55 percent di-, tri- and tetraester, and of 39 percent monoester and 61 percent di-, tri- and tetraester, and sucrose monolaurate;

the products sold under the name Ryoto Sugar Esters, for example referenced B370 and corresponding to sucrose behenate formed of 20 percent monoester and 80 percent diester, triester and polyester;

the sucrose monopalmitate/stearate-dipalmitate/stearate sold by Goldschmidt under the name Tegosoft® PSE.

Preferably, the fatty substances do not comprise any $C_2$-$C_3$ oxyalkylene units or any glycerol units. Preferably, the first fatty substances are not salified fatty acids or soaps, which are water-soluble compounds.

The fatty substances are advantageously chosen from $C_6$-$C_{16}$ hydrocarbons, hydrocarbons containing more than 16 carbon atoms and in particular alkanes, oils of plant origin, fatty acid and/or fatty alcohol esters, and silicones, or mixtures thereof.

Preferably, the fatty substance is an oil (a compound that is liquid at a temperature of 25 degrees centigrade and at atmospheric pressure).

Preferably, the fatty substance is chosen from mineral oil, $C_6$-$C_{16}$ alkanes, polydecenes, liquid fatty acid and/or fatty alcohol esters or their mixtures.

Better still, the fatty substance is chosen from mineral oil, $C_6$-$C_{16}$ alkanes or polydecenes.

Most preferably, the fatty substance is chosen from paraffin oils, petroleum jelly, liquid paraffin, polydecenes, hydrogenated polyisobutene, perfluoromethylcyclopentane, perfluoro-1,3-dimethylcyclohexane, mineral oil, dodecafluoropentane, hexane, dodecane, isohexadecane, isodecane, sunflower oil, maize oil, soya oil, cucurbit oil, grapeseed oil, sesame oil, hazelnut oil, apricot oil, macadamia oil, arara oil, sunflower oil, castor oil, avocado oil, jojoba oil, shea butter oil and mixtures thereof.

The fatty alcohols that may be used in the composition may be chosen from alcohols of formula R'OH, in which R' denotes a saturated or unsaturated, linear or branched radical, comprising from 6 to 40 carbon atoms and more particularly from 8 to 30 carbon atoms. Examples that may be mentioned include cetyl alcohol, stearyl alcohol and the mixture thereof (cetearyl alcohol), octyldodecanol, 2-butyloctanol, 2-hexyldecanol, 2-undecylpentadecanol, oleyl alcohol, lauryl alcohol, behenyl alcohol and linoleyl alcohol.

In certain embodiments, the at least fatty substance is chosen from mineral oil, stearyl alcohol, cetearyl alcohol, cetyl alcohol, and mixtures thereof.

The at least one fatty substance can be employed in the composition of the present invention in an amount of from 1% to 80% by weight, preferably from 1.5% to 60% by weight, more preferably from 2% to 55% by weight, based on the total weight of the composition The fatty substance chosen from oils such as mineral oil, can be employed in the composition of the present invention in an amount of from about 1% to about 70% by weight, preferably from about 1% to about 65% by weight, more preferably from about 1% to about 60% by weight, more preferably from about 1.5% to about 55% by weight, more preferably from about 1.75% to about 50% by weight, more preferably from about 2% to about 45% by weight, based on the total weight of the composition, including all ranges and subranges therebetween.

In certain embodiments, the fatty substance is selected from mineral oil and is employed in the composition of the present invention in an amount of about 1%, 2%, 3%, 4%, 5%, 5.5%, 6%, 6.5%, 7%, 7.5%, 8%, 9%, or 10% by weight, based on the total weight of the composition.

In other embodiments, the fatty substance is selected from mineral oil and is employed in the composition of the present invention in an amount of about 40%, 41%, 42%, 43%, 43.5%, 44%, 44.5%, 45%, 46%, 47%, 48%, 49%, or 50% by weight, based on the total weight of the composition.

The fatty substance chosen from fatty alcohols can be employed in the composition of the present invention in an amount of from about 0.5% to about 30% by weight, preferably from about 1% to about 25% by weight, more preferably from about 2% to about 20% by weight, more preferably from about 2.5% to about 15% by weight, more preferably from about 2.75% to about 12% by weight, more preferably from about 3% to about 10% by weight, based on the total weight of the composition, including all ranges and subranges therebetween.

In certain embodiments, the fatty substance is selected from cetearyl alcohol and is employed in the composition of the present invention in an amount of about 1%, 2%, 3%, 4%, 5%, 5.5%, 6%, 6.5%, 7%, 7.5%, 8%, 9%, or 10% by weight, based on the total weight of the composition.

Nonionic Surfactant

The compositions according to various embodiments of the disclosure also comprise at least one nonionic surfactant chosen from alkoxylated fatty alcohols, alkylpolyglucosides, alkyl(ether)phosphates, and mixtures thereof.

"Alkoxylated fatty alcohol" as used herein means a compound having at least one fatty portion (8 carbon atoms or more) and at least one alkoxylated portion (—$(CH_2)_nO$—, where n is an integer from 1 to 5, preferably 2 to 3). According to particularly preferred embodiments, the alkoxylated fatty alcohols of the present invention can be used as non-ionic surfactants, if desired. In this regard, the alkoxylated fatty alcohols of the present invention preferably have an HLB (hydrophilic-lipophilic balance) value from 1-20, including all ranges and subranges therebetween, with HLB values ranging from 1 to 5 (particularly 3 to 5) or from 15-20 (particularly 16 to 18) being most preferred.

Preferably, the alkoxylated fatty alcohol can be chosen from di-alkyl, tri-alkyl- and combinations of di-alkyl and tri-alkyl substituted ethoxylated polymers. They can also be chosen from mono-alkyl, di-alkyl, tri-alkyl, tetra-alkyl substituted alkyl ethoxylated polymers and all combinations thereof. The alkyl group can be saturated or unsaturated, branched or linear and contain a number of carbon atoms preferably from about 12 carbon atoms to about 50 carbon atoms, including all ranges and subranges therebetween, for example, 20 to 40 carbon atoms, 22 to 24 carbon atoms, 30 to 50 carbon atoms, and 40 to 60 carbon atoms. Most preferably, the fatty portion contains a mixture of compounds of varying carbon atoms such as, for example, C20-C40 compounds, C22-C24 compounds, C30-050 compounds, and C40-C60 compounds.

Preferably, the alkoxylated portion of the alkoxylated fatty alcohols of the present invention contain 2 or more alkoxylation units, preferably from 10 to 200 alkoxylation units, preferably from 20 to 150 alkoxylation units, and preferably from 25 to 100 alkoxylation units, including all ranges and subranges therebetween. Also preferably, the alkoxylation units contain 2 carbon atoms (ethoxylation units) and/or 3 carbon atoms (propoxylation units).

The amount of alkoxylation can also be determined by the percent by weight of the alkoxylated portion with respect to the total weight of the compound. Suitable weight percentages of the alkoxylated portion with respect to the total weight of the compound include, but are not limited to, 10 percent to 95 percent, preferably 20 percent to 90 percent, including all ranges and subranges therebetween with 75 percent to 90 percent (particularly 80 percent to 90 percent) or 20 percent to 50 percent being preferred.

Preferably, the alkoxylated fatty alcohols of the present invention have a number average molecular weight (Mn) greater than 500, preferably from 500 to 5,000, including all ranges and subranges therebetween such as, for example, Mn of 500 to 1250 or an Mn of 2,000 to 5,000.

The alkyl substitution of the alkoxylated fatty alcohol can include mono-alkyl, di-alkyl, tri-alkyl and tetra-alkyl substitution of the polymer and combinations thereof. Suitable examples of mono alkyl substituted polymers include: Steareth-100 available as Brij 700 from Uniqema Inc., Pareth alcohols available as Performathox 450, 480 and 490 available from New Phase Technologies, Inc. Suitable examples of di-alkyl substituted polymers include PEG 120 methyl glucose dioleate available as Glutamate DOE-120 and Glucamate DOE-120 both from Chemron Corporation. Suitable examples of tri-alkyl substituted polymers include PEG 120 methyl glucose trioleate available as Glucamate LT from Chemron Corporation. Suitable examples of tetra-alkyl substituted polymers include PEG 150 pentaerythrityl tetrastearate available as Crothix from Croda Corporation.

Suitable alkoxylated fatty alcohols for use in the present invention include, but are not limited to, alkoxylated C20-C40 fatty alcohols sold under the PERFORMATHOX® name by New Phase Technologies such as, for example, PERFORMATHOX® 420 ETHOXYLATE (Mn=575; 20 percent by weight ethoxylation), PERFORMATHOX® 450 ETHOXYLATE (Mn=920; 50 percent by weight ethoxylation), PERFORMATHOX® 480 ETHOXYLATE (Mn=2300; 80 percent by weight ethoxylation), PERFORMATHOX® 490 ETHOXYLATE (Mn=4600; 90 percent by weight ethoxylation), PERFORMATHOX® 520 ETHOXYLATE (Mn=690; 20 percent by weight ethoxylation), and PERFORMATHOX® 550 ETHOXYLATE (Mn=1100; 50 percent by weight ethoxylation).

Suitable alkyl(ether)phosphates include, but are not limited to, alkoxylated alkyl phosphate esters and alkyl phosphate esters corresponding to a mono-ester of formula (I) and salts thereof:

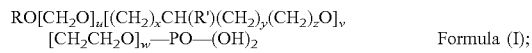
$RO[CH_2O]_u[(CH_2)_xCH(R')(CH_2)_y(CH_2)_zO]_v$
$[CH_2CH_2O]_w$—PO—$(OH)_2$  Formula (I);

a di-ester corresponding to formula (II) and salts thereof:

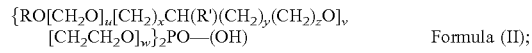
$\{RO[CH_2O]_u[(CH_2)_xCH(R')(CH_2)_y(CH_2)_zO]_v$
$[CH_2CH_2O]_w\}_2PO$—(OH)  Formula (II);

a tri-ester corresponding to formula (III):

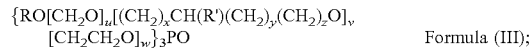
$\{RO[CH_2O]_u[(CH_2)_xCH(R')(CH_2)_y(CH_2)_zO]_v$
$[CH_2CH_2O]_w\}_3PO$  Formula (III);

and combinations thereof, wherein:

R is a hydrocarbon radical containing from 6 to 40 carbon atoms;

u, v and w, independently of one another, represent numbers of from 0 to 60;

x, y and z, independently of one another, represent numbers of from 0 to 13;

R' represents hydrogen, alkyl, the sum of x+y+z being ?0. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formulas (I), (II) and (III), R is linear or branched, acyclic or cyclic, saturated or unsaturated, aliphatic or aromatic, substituted or unsubstituted, preferably a linear or branched, acyclic $C_{6-40}$ alkyl or alkenyl group or a $C_{1-40}$ alkyl phenyl group, more particularly a $C_{8-22}$ alkyl or alkenyl group or a $C_{4-18}$ alkyl phenyl group, more preferably a $C_{12-18}$ alkyl group or alkenyl group or a $C_{6-16}$ alkyl phenyl group; u, v, w, independently of one another, is preferably a number from 2 to 20, more preferably a number from 3 to 17 and most preferably a number from 5 to 15;

x, y, z, independently of one another, is preferably a number from 2 to 13, more preferably a number from 1 to 10 and most preferably a number from 0 to 8.

In general, the lower the number of carbon atoms in the R group of the phosphate esters, the more irritating to the skin and the less soluble in water the phosphate ester becomes. In contrast, the higher the number of carbon atoms in the R group, the milder to the skin and the thicker and more waxy the resultant product becomes. Accordingly, for best results, R should have from 12 to 18 carbon atoms.

Examples of alkylpolyglucosides are decyl glucoside and lauryl glucoside.

Particularly preferred alkoxylated alkyl phosphate esters for use in the present invention are PPG-5-Ceteth-10 phosphate (CRODAFOS SG®), Oleth-3 phosphate (CRODAFOS N3 acid), Oleth-10 phosphate (CRODAFOS N10 acid), and a mixture of Ceteth-10 phosphate and Dicetyl phosphate (CRODAFOS CES) all sold by Croda. Particularly preferred alkyl phosphate esters are Cetyl phosphate (Hostaphat CC 100), Stearyl phosphate (Hostaphat CS 120) from Clariant.

In the present invention, the at least one nonionic surfactant chosen from alkoylated fatty alcohols can be employed in the composition of the present invention in an amount of from about 0.1% to about 20% by weight, such as from about 0.5% to about 18% by weight, or such as from about 1% to about 15% by weight, or such as from about 1.5% to about 12%, or such as from about 2% to about 10% by weight, preferably from about 2.25% to about 8% by weight, preferably from about 2.5% to about 6% by weight, and most preferably from about 2.5% to about 5% by weight, based on the weight of the composition as a whole, including all ranges and subranges within these ranges.

In certain embodiments, the at least one nonionic surfactant chosen from alkoylated fatty alcohols and alkyl(ether) phosphates is selected from PPG-5-Ceteth-10 phosphate, Ceteth-10 phosphate and Dicetyl phosphate, and is employed in the composition of the present invention in an amount of about 1%, 2%, 2.25%, o 2.5%, 2.75%, 3%, 3.25%, 3.5%, 3.75%, 4%, 4.25%, 4.5%, 4.75%, 5%, 5.25%, or 5.5% by weight, based on the total weight of the composition.

Quaternary Ammonium Compound

The compositions according to the present invention may also comprise at least one quaternary ammonium compound. This compound may be in the form of a cationic polymer or in the form of a quaternary ammonium salt.

The quaternary ammonium compound may be chosen from cationic associative polymers comprising, in their structure, a pendent or terminal hydrophobic chain, for example of alkyl or alkenyl type, containing from 10 to 30 carbon atoms.

The quaternary ammonium compound of the compositions can also be chosen from, for example:

(1) homopolymers and copolymers derived from acrylic or methacrylic esters or amides, examples of which are:

copolymers of acrylamide and of dimethylaminoethyl acrylate quaternized with dimethyl sulfate or with a dimethyl halide, such as the product sold under the name HERCOFLOC by the company Hercules, the copolymers of acrylamide and of methacryloyloxy-ethyltrimethylammonium chloride described, for example, in EP 80 976 and sold under the name BINA QUAT P 100 by the company Ciba Geigy, the copolymer of acrylamide and of methacryloyloxyethyltrimethylammonium methosulfate sold under the name RETEN by the company Hercules, quaternized or non-quaternized vinylpyrrolidone/dialkylaminoalkyl acrylate or acrylate copolymers, such as the products sold under the name GAFQUAT by the company ISP, for instance GAFQUAT 734 or GAFQUAT 755, or alternatively the products known as COPOLYMER 845, 958 and 937, dimethylaminoethyl acrylate/vinylcaprolactam/vinylpyrrolidone terpolymers, such as the product sold under the name GAFFIX VC 713 by the company ISP, vinylpyrrolidone/methacrylamidopropyldimethylamine copolymers sold, for example, under the name STYLEZE CC 10 by ISP, quaternized vinylpyrrolidone/dimethylami nopropyl-methacrylamide copolymers such as the product sold under the name GAFQUAT HS 100 by the company ISP, and crosslinked polymers of methacryloyloxy($C_1$-$C_4$)alkyltri ($C_1$-$C_4$)alkylammonium salts such as the polymers obtained by homopolymerization of dimethylaminoethyl acrylate quaternized with methyl chloride, or by copolymerization of acrylamide with dimethylaminoethyl acrylate quaternized with methyl chloride, the homo- or copolymerization being followed by crosslinking with a compound containing olefinic unsaturation, such as methylenebisacrylamide. In at least one embodiment, a crosslinked acrylamide/methacryloyloxyethyltrimethylammonium chloride copolymer (20/80 by weight) in the form of a dispersion containing 50 percent by weight of the copolymer in mineral oil can be used. This dispersion is sold under the name SALCARE® SC 92 by the company Ciba. In some embodiments, a crosslinked methacryloyloxyethyltrimethylammonium chloride homopolymer containing about 50 percent by weight of the homopolymer in mineral oil or in a liquid ester can be used. These dispersions are sold under the names SALCARE® SC 95 and SALCARE® SC 96 by the company Ciba.

Other examples are cellulose ether derivatives comprising quaternary ammonium groups, such as the polymers sold under the names JR (JR 400, JR 125, JR 30M) or LR (LR 400, LR 30M) by the company Union Carbide Corporation.

(2) copolymers of cellulose or cellulose derivatives grafted with a water-soluble quaternary ammonium monomer, such as hydroxymethyl-, hydroxyethyl- or hydroxypropylcelluloses grafted, for instance, with a methacryloylethyltrimethylammonium, methacrylamidopropyltrimethylammonium or dimethyldiallylammonium salt. These are sold under the name CELQUAT L 200 and CELQUAT H 100 by the company National Starch.

(3) non-cellulose cationic polysaccharides, such as guar gums containing trialkylammonium cationic groups. Such products are sold, for example, under the trade names JAGUAR C13S, JAGUAR C15, JAGUAR C17 and JAGUAR C162 by the company Meyhall.

(4) polymers of piperazinyl units and of divalent alkylene or hydroxyalkylene radicals.

(5) water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in an amount ranging from 0.025 to 0.35 mol per amine group of the polyamino amide; these polyamino amides can be alkylated or, if they contain at least one tertiary amine function, they can be quaternized. Exemplary mention may be made of the adipic acid/dimethylaminohydroxypropyl/diethylenetriamine polymers sold under the name CARTARETINE F, F4 or F8 by the company Sandoz.

(6) the polymers obtained by reaction of at least one polyalkylene polyamine containing two primary amine groups and at least one secondary amine group with a dicarboxylic acid chosen from diglycolic acid and saturated $C_3$-$C_8$ aliphatic dicarboxylic acids. The molar ratio between the polyalkylene polyamine and the dicarboxylic acid ranges from 0.8:1 to 1.4:1; the polyamino amide resulting therefrom is reacted with epichlorohydrin in a molar ratio of epichlorohydrin relative to the secondary amine group of the polyamino amide ranging from 0.5:1 to 1.8:1. Polymers of this type are sold, for example, under the name HERCOSETT 57, PD 170 or DELSETTE 101 by the company Hercules.

(7) cyclopolymers of alkyldiallylamine and of dialkyldiallylammonium, such as for example: dimethyldiallylammonium chloride homopolymer sold under the name MERQUAT® 100 and MERQUAT® 280 by the company Nalco (and its homologues of low weight-average molecular mass) and the copolymers of diallyldimethylammonium chloride and of acrylamide, sold under the name MERQUAT® 550.

(8) quaternary diammonium polymers.

(9) polyquaternary ammonium polymers; examples that may be mentioned include the products MIRAPOL A 15, MIRAPOL AD1, MIRAPOL AZ1 and MIRAPOL 175 sold by the company Miranol.

(10) quaternary polymers of vinylpyrrolidone and of vinylimidazole, for instance the products sold under the names LUVIQUAT FC 905, FC 550 and FC 370 by the company BASF.

(11) vinylamide homopolymers or copolymers, such as partially hydrolysed vinylamide homopolymers such as poly(vinylamine/vinylamide)s.

(12) cationic polyurethane derivatives, for example those of elastic nature formed from the reaction:

(a1) of at least one cationic unit resulting from at least one tertiary or quaternary amine bearing at least two reactive functions containing labile hydrogen, (a2) of at least one mixture of at least two different nonionic units bearing at least two reactive functions containing labile hydrogen, for instance chosen from hydroxyl groups, primary or secondary amine groups, and thiol groups, and (b) of at least one compound comprising at least two isocyanate functions.

(13) Other quaternary ammonium compound that may be used in the context of the disclosure include, for example, cationic proteins or cationic protein hydrolysates, polyalkyleneimines, such as polyethyleneimines, polymers containing vinylpyridine or vinylpyridinium units, and chitin derivatives.

Particularly useful quaternary ammonium compound in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxypropyltrimonium chloride.

Particularly preferred quaternary ammonium compound of the present invention include SOFTCAT POLYMER SL-100 (Polyquaternium-67) available from AMERCHOL; POLYMER JR-125, POLYMER JR-400, Polymer JR-30M hydroxyethyl cellulosic polymers (polyquaternium 10) available from AMERCHOL; JAGUAR C® 13-S, guar hydroxypropyltrimonium chloride, available from Rhodia; and MERQUAT® 100 and 280, a dimethyl dialkyl ammonium chloride (polyquaternium 6) available from Nalco.

In other embodiments, the quaternary ammonium compound may be chosen from a quaternary ammonium salt and a quaternary diammonium salt.

Suitable examples of quaternary ammonium salts are tetraalkylammonium chlorides, for instance dialkyldimethylammonium or alkyltrimethylammonium chlorides in which the alkyl group contains approximately from 12 to 22 carbon atoms, in particular behenyltrimethylammonium chloride, distearyldimethylammonium chloride, cetyltrimethylammonium chloride, benzyldimethylstearylammonium chloride, or else, secondly, distearoylethylhydroxyethylmethylammonium methosulfate, dipalmitoylethylhydroxyethyl-ammonium methosulfate or distearoylethylhydroxyethylammonium methosulfate, or else, lastly, palmitylamidopropyltrimethylammonium chloride or stearamidopropyl-dimethyl(myristyl acetate) ammonium chloride, sold under the name Ceraphyl® 70 by the company Van Dyk.

Other types of quaternary ammonium salts for use according to the invention are quaternary ammonium salts of imidazoline, di- or triquaternary ammonium salts, and quaternary ammonium salts containing one or more ester functions.

Examples of quaternary ammonium salts that may especially be mentioned include:

those corresponding to the general formula below:

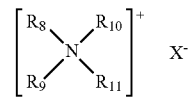

in which the groups R8 to R11, which may be identical or different, represent a linear or branched aliphatic group containing from 1 to 30 carbon atoms, or an aromatic group such as aryl or alkylaryl, at least one of the groups R8 to R11 denoting a group containing from 8 to 30 carbon atoms, preferably from 12 to 24 carbon atoms. The aliphatic groups may comprise heteroatoms such as, in particular, oxygen, nitrogen, sulfur and halogens. The aliphatic groups are chosen, for example, from C1-30 alkyl, C1-30 alkoxy, polyoxy(C2-C6)alkylene, C1-30 alkylamide, (C12-C22)alkylamido(C2-C6)alkyl, (C12-C22)alkylacetate and C1-30 hydroxyalkyl; X- is an anion chosen from the group of halides, phosphates, acetates, lactates, (C1-C4)alkyl sulfates, and (C1-C4)alkyl- or (C1-C4)alkylaryl-sulfonates.

Among the quaternary ammonium salt, those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, the palmitylamidopropyltrimethylammonium salt, the stearamidopropyltrimethylammonium salt, the stearamidopropyldimethylcetearylammonium salt, or the stearamidopropyldimethyl(myristyl acetate)ammonium salt sold under the name Ceraphyl® 70 by the company Van Dyk. It is particularly preferred to use the chloride salts of these compounds;

quaternary ammonium salts of imidazoline, for instance those of the formula below:

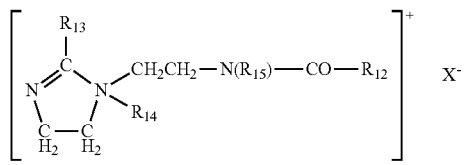

in which R12 represents an alkyl or alkenyl group containing from 8 to 30 carbon atoms, derived for example from tallow fatty acids, R13 represents a hydrogen atom, a C1-C4 alkyl group or an alkyl or alkenyl group containing from 8 to 30 carbon atoms, R14 represents a C1-C4 alkyl group, R15 represents a hydrogen atom or a C1-C4 alkyl group, X- is an anion selected from the group consisting of halides, phosphates, acetates, lactates, alkyl sulfates, alkylsulfonates or alkylarylsulfonates in which the alkyl and aryl groups each preferably comprise from 1 to 20 carbon atoms and from 6 to 30 carbon atoms. R12 and R13 preferably denote a mixture of alkyl or alkenyl groups comprising from 12 to 21 carbon atoms, for example tallow fatty acid derivatives, R14 denotes a methyl group, and R15 denotes a hydrogen atom. Such a product is sold, for example, under the name Rewoquat® W 75 by the company Rewo;

quaternary diammonium or triammonium salts, in particular of the following formula:

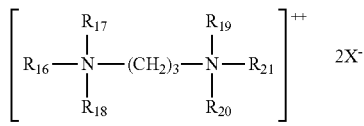

in which R16 denotes an alkyl radical containing approximately from 16 to 30 carbon atoms, which is optionally hydroxylated and/or interrupted by one or more oxygen atoms, R17 is selected from hydrogen and an alkyl radical containing from 1 to 4 carbon atoms or a group (R16a)(R17a)(R18a)N—(CH2)3, R16a, R1m, R18a, R18, R19, R20 and R21, which are identical or different, are selected from hydrogen and an alkyl radical containing from 1 to 4 carbon atoms, and X- is an anion selected from the group of halides, acetates, phosphates, nitrates and methyl sulfates. Such compounds are, for example, Finquat CT-P, available from the company Finetex (Quaternium 89), and Finquat CT, available from the company Finetex (Quaternium 75), quaternary ammonium salts containing at least one ester function, such as those of the formula below:

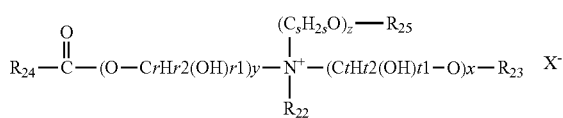

in which:
R22 is selected from C1-C6 alkyl groups and C1-C6 hydroxyalkyl or dihydroxyalkyl groups;
R23 is selected from:
the group

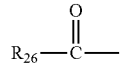

groups R27, which are linear or branched, saturated or unsaturated C1-C22 hydrocarbon-based groups,
a hydrogen atom,
R25 is selected from:
the group

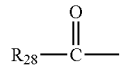

groups R29, which are linear or branched, saturated or unsaturated C1-C6 hydrocarbon-based groups,
a hydrogen atom,
R24, R26 and R28, which are identical or different, are selected from linear or branched, saturated or unsaturated C7-C21 hydrocarbon radicals;
r, s and t, which may be identical or different, are integers ranging from 2 to 6;
r1 and t1, which may be identical or different, are equal to 0 or 1, and r2+r1=2r and t1+t2=2t;
y is an integer ranging from 1 to 10;
x and z, which may be identical or different, are integers ranging from 0 to 10;
X- is a simple or complex, organic or inorganic anion;
with the proviso that the sum x+y+z is from 1 to 15, that when x is 0, then R23 denotes R27 and that when z is 0, then R25 denotes R29.

The alkyl groups R22 may be linear or branched, and more particularly linear.

Preferably, R22 denotes a methyl, ethyl, hydroxyethyl or dihydroxypropyl group, and more particularly a methyl or ethyl group.

Advantageously, the sum x+y+z is from 1 to 10.

When R23 is a hydrocarbon-based group R27, it may be long and may have 12 to 22 carbon atoms, or may be short and may have from 1 to 3 carbon atoms.

When R25 is a hydrocarbon-based group R29, it preferably contains 1 to 3 carbon atoms.

Advantageously, R24, R26 and R28, which may be identical or different, are chosen from linear or branched, saturated or unsaturated C11-C21 hydrocarbon-based groups, and more particularly from linear or branched, saturated or unsaturated C11-C21 alkyl and alkenyl groups.

Preferably, x and z, which may be identical or different, are equal to 0 or 1.

y is advantageously equal to 1.

Preferably, r, s and t, which may be identical or different, equal 2 or 3, and even more particularly are equal to 2.

The anion X- is preferably a halide (chloride, bromide or iodide) or an alkyl sulfate, more particularly methyl sulfate. However, it is possible to use methanesulfonate, phosphate, nitrate, tosylate, an anion derived from an organic acid, such as acetate or lactate, or any other anion that is compatible with the ammonium containing an ester function.

The anion X- is even more particularly chloride or methyl sulfate.

Use is made more particularly, in the composition according to the invention, of the ammonium salts of formula (XII) in which:
R22 denotes a methyl or ethyl group,
x and y are equal to 1;
z is equal to 0 or 1;
r, s and t are equal to 2;
R23 is selected from:
the group methyl, ethyl or C14-C22 hydrocarbon-based groups,
a hydrogen atom,
R25 is selected from:
the group

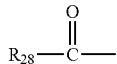

a hydrogen atom,

R24, R26 and R28, which may be identical or different, are chosen from linear or branched, saturated or unsaturated C13-C17 hydrocarbon-based groups, and preferably from linear or branched, saturated or unsaturated C13-C17 alkyl and alkenyl groups.

The hydrocarbon-based groups are advantageously linear.

Mention may be made, for example, of the compounds such as the diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, of triisopropanolamine, of an alkyldiethanolamine or of an alkyldiisopropanolamine, which are optionally oxyalkylenated, with C10-C30 fatty acids or with mixtures of C10-C30 fatty acids of plant or animal origin, or by transesterification of the methyl esters thereof. This esterification is followed by a quaternization using an alkylating agent such as an alkyl halide (preferably a methyl or ethyl halide), a dialkyl sulfate (preferably a dimethyl or diethyl sulfate), methyl methanesulfonate, methyl para-toluenesulfonate, glycol chlorohydrin or glycerol chlorohydrin.

Such compounds are sold, for example, under the names DEHYQUART by the company Henkel, STEPANQUART by the company STEPAN NOXAMIUM by the company Ceca or REQOQUAT WE 18 by the company Rewo-Witco.

The composition according to the invention may contain, for example, a mixture of quaternary ammonium monoester, diester and triester salts with a weight majority of diester salts.

It is also possible to use the ammonium salts containing at least one ester function that are described in patents U.S. Pat. Nos. 4,874,554 and 4,137,180.

Use may be made of behenoylhydroxypropyltrimethylammonium chloride sold by KAO under the name Quatarmin BTC 131.

Preferably, the ammonium salts containing at least one ester function contain two ester functions.

Among the quaternary ammonium salts containing at least one ester function, which can be used, it is preferred to use dipalmitoylethylhydroxyethylmethylammonium salts.

In preferred embodiments, the quaternary ammonium compound of the present invention is chosen from polyquaternium-6, polyquaternium-10, polyquaternium-67, and mixtures thereof.

In other preferred embodiments, the quaternary ammonium compound of the present invention is chosen from polyquaternium-6, polyquaternium-67, and mixtures thereof.

In yet preferred embodiments, the quaternary ammonium compound of the present invention is chosen from polyquaternium-6.

In the present invention, the quaternary ammonium compound may be employed in the composition of the present invention in an amount of from about 0% to about 10% by weight, preferably from about 0.1% to about 8% by weight, preferably from about 0.5% to about 5% by weight, preferably from about 0.75% to about 4%, preferably from about 1% to about 3% by weight, based on the weight of the composition as a whole, including all ranges and subranges within these ranges.

In certain embodiments, the quaternary ammonium compound is selected from Polyquaternium-6, Polyquaternium-10, and Polyquaternium-67, and is employed in the composition of the present invention in an amount of about 0.5%, or about 1%, or about 1.25%, or about 1.5%, or about 1.75%, or about 2%, or about 2.25%, or about 2.5%, or about 2.75%, or about 3%, or about 3.25%, or about 3.5%, or about 3.75%, or about 4%, or about 4.25%, or about 4.5% by weight, based on the total weight of the composition.

In other embodiments, the quaternary ammonium compound is not present in the inventive composition.

Silicone Compounds

The silicones that can be used in the cosmetic composition of the present invention are volatile or non-volatile, cyclic, linear or branched silicones, which are unmodified or modified with organic groups, having a viscosity from $5 \times 10^{-6}$ to $2.5$ m$^2$/s at 25 degrees centigrade, and preferably $1 \times 10^{-5}$ to $1$ m$^2$/s.

The silicones which can be used in accordance with the invention can be provided in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from poly(oxyalkylene) groups, amino groups and alkoxy groups.

Organopolysiloxanes are defined in more detail in Walter Noll's "Chemistry and Technology of Silicones" (1968), Academic Press. They can be volatile or non-volatile.

When they are volatile, the silicones are more particularly chosen from those having a boiling point of between 60 degrees centigrade and 260 degrees centigrade, and more particularly still from:

(i) cyclic polydialkylsiloxanes comprising from 3 to 7 and preferably from 4 to 5 silicon atoms. They are, for example, octamethylcyclotetrasiloxane, sold in particular under the name Volatile Silicone® 7207 by Union Carbide or Silbione® 70045 V2 by Rhodia, decamethylcyclopentasiloxane, sold under the name Volatile Silicone® 7158 by Union Carbide and Silbione® 70045 V5 by Rhodia, and mixtures thereof.

Mention may also be made of cyclocopolymers of the dimethylsiloxane/methylalkylsiloxane type, such as Volatile Silicone® FZ 3109, sold by Union Carbide, having the formula:

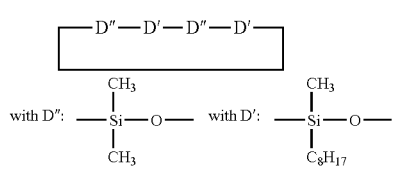

Mention may also be made of mixtures of cyclic polydialkylsiloxanes with organic compounds derived from silicon, such as the mixture of octamethylcyclotetrasiloxane and tetra(trimethylsilyl)pentaerythritol (50/50) and the mixture of octamethylcyclotetrasiloxane and oxy-1,1'-bis(2,2,2', 2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25 degrees centigrade An example is decamethyltetrasiloxane sold in particular under the name SH 200 by the company Toray Silicone. Silicones coming within this category are also described in the paper published in Cosmetics and Toiletries, Vol. 91, January 76, pp. 27-32, Todd and Byers, Volatile Silicone Fluids for Cosmetics.

Use is preferably made of non-volatile polydialkylsiloxanes, polydialkylsiloxane gums and resins, polyorganosiloxanes modified with the organofunctional groups above, and mixtures thereof.

These silicones are more particularly chosen from polydialkylsiloxanes, among which mention may be made mainly of polydimethylsiloxanes having trimethylsilyl end groups. The viscosity of the silicones is measured at 25 degrees centigrade according to Standard ASTM 445 Appendix C.

Mention may be made, among these polydialkylsiloxanes, without implied limitation, of the following commercial products:

the Silbione® oils of the 47 and 70 047 series or the Mirasil® oils sold by Rhodia, such as, for example, the oil 70 047 V 500 000;

the oils of the Mirasil® series sold by Rhodia;

the oils of the 200 series from Dow Corning, such as DC200 having a viscosity of 60 000 mm$^2$/s;

the Viscasil® oils from General Electric and certain oils of the SF series (SF 96, SF 18) from General Electric.

Mention may also be made of polydimethylsiloxanes having dimethylsilanol end groups known under the name of dimethiconol (CTFA), such as the oils of the 48 series from Rhodia.

Mention may also be made, in this category of polydialkylsiloxanes, of the products sold under the names Abil Wax® 9800 and 9801 by Goldschmidt, which are polydi($C_1$-$C_{20}$)alkylsiloxanes.

The silicone gums which can be used in accordance with the invention are in particular polydialkylsiloxanes and preferably polydimethylsiloxanes having high number-average molecular weights of between 200,000 and 1,000,000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane, tridecane or their mixtures.

Products which can be used more particularly in accordance with the invention are mixtures, such as:

the mixtures formed from a polydimethylsiloxane hydroxylated at the chain end, or dimethiconol (CTFA), and from a cyclic polydimethylsiloxane, also known as cyclomethicone (CTFA), such as the product Q2 1401 sold by Dow Corning;

the mixtures of a polydimethylsiloxane gum and of a cyclic silicone, such as the product SF 1214 Silicone Fluid from General Electric; this product is an SF 30 gum corresponding to a dimethicone, having a number-average molecular weight of 500 000, dissolved in the oil SF 1202 Silicone Fluid corresponding to decamethylcyclopentasiloxane;

the mixtures of two PDMSs with different viscosities, and more particularly of a PDMS gum and a PDMS oil, such as the product SF 1236 from General Electric. The product SF 1236 is the mixture of a gum SE 30 defined above having a viscosity of 20 m$^2$/s and of an oil SF 96 with a viscosity of $5 \times 10^{-6}$ m$^2$/s. This product preferably comprises 15 percent of gum SE 30 and 85 percent of an oil SF 96.

The organopolysiloxane resins which can be used in accordance with the invention are crosslinked siloxane systems including the following units:

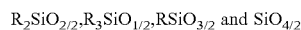

in which R represents an alkyl having from 1 to 16 carbon atoms. Among these products, those that are particularly preferred are those in which R denotes a lower $C_1$-$C_4$alkyl group, more particularly methyl.

Mention may be made, among these resins, of the product sold under the name Dow Corning 593 or those sold under the names Silicone Fluid SS 4230 and SS 4267 by General Electric, which are silicones of dimethyl/trimethylsiloxane structure.

Mention may also be made of the resins of the trimethylsiloxysilicate type, sold in particular under the names X22-4914, X21-5034 and X21-5037 by Shin-Etsu.

The organomodified silicones which can be used in accordance with the invention are silicones as defined above comprising, in their structure, one or more organofunctional groups attached via a hydrocarbon group.

In addition to the silicones described above, the organomodified silicones can be polydiarylsiloxanes, in particular polydiphenylsiloxanes, and polyalkylarylsiloxanes functionalized by the abovementioned organo functional groups.

The polyalkylarylsiloxanes are chosen in particular from linear and/or branched polydimethyl/methylphenylsiloxanes and polydimethyl/diphenylsiloxanes with a viscosity ranging from $1 \times 10^{-5}$ to $5 \times 10^{-2}$ m$^2$/s at 25 degrees centigrade Among these polyalkylarylsiloxanes, examples that may be mentioned include the products sold under the following names:

Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Mention may be made, among the organomodified silicones, of polyorganosiloxanes comprising:

polyethyleneoxy and/or polypropyleneoxy groups optionally comprising $C_6$-$C_{24}$ alkyl groups, such as the products named dimethicone copolyol sold by Dow Corning under the name DC 1248 or the oils Silwet® L 722, L 7500, L 77 and L 711 by Union Carbide, and the ($C_{12}$)alkyl methicone copolyol sold by Dow Corning under the name Q2 5200;

substituted or unsubstituted amino groups, such as the products sold under the names GP 4 Silicone Fluid and GP 7100 by Genesee or the products sold under the names Q2 8220 and Dow Corning 929 or 939 by Dow Corning. The substituted amino groups are in particular $C_1$-$C_4$ aminoalkyl groups;

alkoxylated groups, such as the product sold under the name Silicone Copolymer F-755 by SWS Silicones, and Abil Wax® 2428, 2434 and 2440 by Goldschmidt.

The silicone compounds of the present invention can also be chosen from dimethicone copolyols.

Dimethicone Copolyol, as used herein, includes a polymer made from dimethicone and polyoxyethylene and/or polyoxypropylene.

Suitable examples of dimethicone copolyols include Dimethicone PEG-Adipate, Dimethicone PEG-8 Benzoate, Dimethicone PEG-7 Phosphate, Dimethicone PEG-8 Phosphate, Dimethicone PEG-10 Phosphate, Dimethicone PEG/PPG-20/23 Benzoate, Dimethicone PEG/PPG-7/4 Phosphate, Dimethicone PEG/PPG-12/4 Phosphate, PEG-3 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-6/11 Dimethicone, PEG/PPG-8/14 Dimethicone, PEG/PPG-14/4 Dimethicone, PEG/PPG-15/15 Dimethicone, PEG/PPG-16/2 Dimethicone, PEG/PPG-17/18 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, and mixtures thereof.

Dimethicone copolyols can also be described as silicone surfactants or as emulsifiers.

Thus, the dimethicone copolyol employed according to the invention is advantageously an oxypropylenated and/or oxyethylenated polydimethyl(methyl)siloxane. Use may be made, as dimethicone copolyol, of those corresponding to the following formula (I):

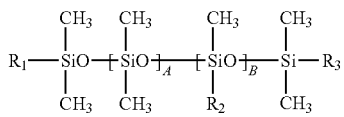

(I)

in which:

$R_1$, $R_2$ and $R_3$ represent, independently of one another, a $C_1$-$C_6$ alkyl radical or a —(CH2)x-(OCH2CH2)y-(OCH2CH2CH2)z-OR4 radical, at least one Rb $R_2$ or $R_3$ radical not being an alkyl radical; $R_4$ being a hydrogen, a $C_1$-$C_3$ alkyl radical or a $C_2$-$C_4$ acyl radical;

A is an integer ranging from 0 to 200;

B is an integer ranging from 0 to 50; provided that A and B are not equal to zero at the same time; x is an integer ranging from 1 to 6; y is an integer ranging from 1 to 30; z is an integer ranging from 0 to 5.

According to a preferred embodiment of the invention, in the compound of formula (I), R=$R_3$=methyl radical, x is an integer ranging from 2 to 6 and y is an integer ranging from 4 to 30. $R_4$ is in particular a hydrogen.

Mention may be made, as examples of compounds of formula (I), of the compounds of formula (II):

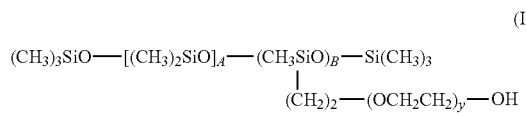

(II)

in which A is an integer ranging from 20 to 105, B is an integer ranging from 2 to 10 and y is an integer ranging from 10 to 20.

Mention may also be made, as examples of silicone compounds of formula (I), of the compounds of formula (III):

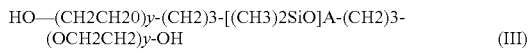

(III)

in which A' and y are integers ranging from 10 to 20.

Use may be made, as dimethicone copolyol, of those sold under the names DC 5329, DC 7439-146, DC 2-5695 and Q4-3667 by Dow Corning; and KF-6013, KF-6015, KF-6016, KF-6017 and KF-6028 by Shin-Etsu.

In an embodiment, the compositions of the invention comprise as dimethicone copolyol one of those sold under the names KF-6013, KF-6015, KF-6016, KF-6017 and KF-6028 by Shin-Etsu.

In another embodiment, the dimethicone copolyol in the compositions of the invention is chosen from PEG-12 dimethicone commercially available from Dow Corning under the trade name XIAMETER® OFX-0193 FLUID.

The dimethicone copolyols in the compositions of the invention can also be chosen from at least one C8-C22 alkyl dimethicone copolyol.

This C8-C22 alkyl dimethicone copolyol of the invention is more particularly an oxypropylenated and/or oxyethylenated polymethyl (C8-C22) alkyl dimethyl methyl siloxane.

The C8-C22 alkyl dimethicone copolyol is advantageously a compound of the following formula (IV):

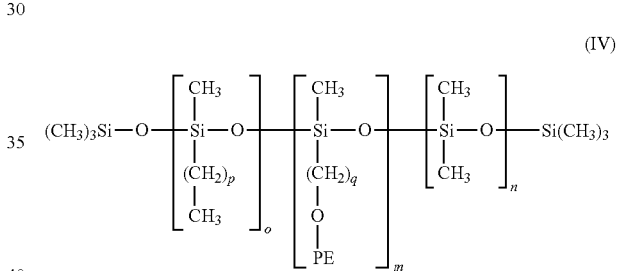

(IV)

wherein:

PE represents from groups (—C2H40)x-(C3H60)y-R, wherein R is chosen from a hydrogen atom and an alkyl radical comprising from 1 to 4 carbon atoms, x is an integer ranging from 0 to 100, and y is an integer ranging from 0 to 80, provided that x and y are not simultaneously equal to 0; and m is an integer ranging from 1 to 40, n is an integer ranging from 10 to 200, o is an integer ranging from 1 to 100, p is an integer ranging from 7 to 21, and q is an integer ranging from 0 to 4.

Preferably, R is a hydrogen atom, m is an integer ranging from 1 to 10, n is an integer ranging from 10 to 100, o is an integer ranging from 1 to 30, p is 15, and q is 3. In a preferred embodiment the at least one C8-C22 alkyl dimethicone copolyol of the present invention is chosen from cetyl dimethicone copolyols such as the product marketed under the name Abil® EM-90 by the company Goldschmidt.

In one embodiment, the C8-C22 alkyl dimethicone copolyol is a cetyl dimethicone copolyol, and more particularly the product marketed under the name Abil® EM-90 by the company Goldschmidt (also known as cetyl PEG/PPG-10/1 dimethicone).

In another embodiment, the compositions of the invention comprise cetyl PEG/PPG-10/1 dimethicone as C8-C22 alkyl dimethicone copolyol and a mixture of dimethicone and dimethicone/vinyl dimethicone crosspolymer as organopolysiloxane elastomer not containing a hydrophilic chain.

In another preferred embodiment, the compositions of the invention comprise a mixture of dimethicone and dimethicone/vinyl dimethicone crosspolymer as organopolysiloxane elastomer not containing a hydrophilic chain, a PEG-10 dimethicone as dimethicone copolyol, and a cetyl PEG/PPG-10/1 dimethicone as C8-C22 alkyl dimethicone copolyol.

Thus, in certain embodiments, the dimethicone copolyol in the present invention is chosen from oxypropylenated and/or oxyethylenated polydimethyl(methyl)siloxane, oxypropylenated and/or oxyethylenated polymethyl (C8-C22) alkyl dimethyl methyl siloxane, and mixtures thereof.

In certain other embodiments, the dimethicone copolyol is chosen from Dimethicone PEG-8 Benzoate, Dimethicone PEG-7 Phosphate, Dimethicone PEG-8 Phosphate, Dimethicone PEG-10 Phosphate, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-17/18 Dimethicone, cetyl PEG/PPG-10/1 dimethicone, and mixtures thereof. In other embodiments, the dimethicone copolyol is preferably PEG-12 dimethicone, The silicone compounds are generally present in the composition in a proportion as active material (AM) ranging from about 0.1% to about 10% by weight, preferably from about 0.5% to about 8% by weight, more preferably from about 0.5% to about 5% by weight, even more preferably from about 1% to about 3% by weight, based on the total weight of the composition, including all ranges and subranges therebetween.

In certain embodiments, the silicone compound is chosen from dimethicone copolyol and is employed in the compositions of the present invention in an amount of about 0.1%, or about 0.25%, or about 0.5%, or about 0.75%, or about 1% by weight, or about 1.1%, or about 1.2%, or about 1.3%, or about 1.4% by weight, or about 1.5% by weight, or about 1.6%, or about 1.7%, or about 1.8%, or about 1.9% by weight, or about 2% by weight, or about 3% by weight, or about 4% by weight, or about 5% by weight, based on the total weight of the composition.

Thickening Agents

The compositions according to various embodiments of the disclosure comprise at least one component chosen from thickening agents, also referred to interchangeably herein as thickeners or rheology modifiers. Thickening agents are generally used to modify the viscosity or rheology of compositions. Non-limiting examples of thickening agents that may be used according to various embodiments of the disclosure include those conventionally used in cosmetics, such as polymers of natural origin and synthetic polymers. For example, nonionic, anionic, cationic, amphiphilic, and amphoteric polymers, and other known rheology modifiers, such as cellulose-based thickeners, may be chosen.

The thickening agents may be chosen from, for example, hydrophilic thickeners, for example cellulose polymers and gums. As used herein, the term "hydrophilic thickener" is meant to indicate that the thickening agent is soluble or dispersible in water. Non-limiting examples of hydrophilic thickeners include modified or unmodified carboxyvinyl polymers, such as the products sold under the name CARBOPOL (CTFA name: carbomer) by Goodrich, homopolymers or copolymers of acrylic or methacrylic acids or the salts thereof and the esters thereof, such as the products sold under the names VERSICOL F® or VERSICOL K® by Allied Colloid, ULTRAHOLD 8® by Ciba-Geigy, polyacrylates and polymethacrylates such as the products sold under the names LUBRAJEL and NORGEL by Guardian, or under the name HISPAJEL by Hispano Chimica, and polyacrylic acids of SYNTHALEN K type, polyacrylamides, copolymers of acrylic acid and of acrylamide sold in the form of the sodium salt thereof, such as under the names RETEN® by Hercules, the sodium polymethacrylate such as sold under the name DARVAN 7® by Vanderbilt, and the sodium salts of polyhydroxycarboxylic acids such as sold under the name HYDAGEN F® by Henkel, optionally crosslinked and/or neutralized 2-acrylamido-2-methylpropanesulphonic acid polymers and copolymers, for instance poly(2-acrylamido-2-methylpropanesulphonic acid) such as sold by Clariant under the name HOSTACERIN AMPS (CTFA name: ammonium polyacryldimethyltauramide), crosslinked anionic copolymers of acrylamide and of AMPS, e.g. in the form of a water-in-oil emulsion, such as those sold under the name SEPIGEL™ 305 (CTFA name: Polyacrylamide/C13-14 Isoparaffin/Laureth-7) and under the name SIMULGEL™ 600 (CTFA name: Acrylamide/Sodium acryloyldimethyltaurate copolymer/Isohexadecane/Polysorbate 80) by SEPPIC, polyacrylic acid/alkyl acrylate copolymers of PEMULEN type, associative polymers, for instance PEG-150/stearyl alcohol/SMDI copolymer such as sold under the name ACULYN™ 46 by Rohm & Haas, steareth-100/PEG-136/HDI copolymer such as sold under the name RHEOLATE® FX 1100 by Elementis), as well as mixtures thereof.

Other exemplary hydrophilic thickeners include associative polymers. As used herein, the term "associative polymer" is intended to mean any amphiphilic polymer comprising in its structure at least one fatty chain and at least one hydrophilic portion. The associative polymers in accordance various exemplary embodiments may be anionic, cationic, nonionic or amphoteric. By way of example, associative polymers which may be chosen include those comprising at least one hydrophilic unit and at least one fatty-chain allyl ether unit, such as those in which the hydrophilic unit is constituted of an ethylenic unsaturated anionic monomer, such as a vinylcarboxylic acid or an acrylic acid, a methacrylic acid, and mixtures thereof, and in which the fatty-chain allyl ether unit corresponds to the monomer of formula (I) below:

$$CH_2=C(R')CH_2OB_nR \qquad (I)$$

in which R' is chosen from H or $CH_3$, B is chosen from an ethyleneoxy radical, n is zero or is chosen from an integer ranging from 1 to 100, and R is chosen from a hydrocarbon-based radical chosen from alkyl, arylalkyl, aryl, alkylaryl and cycloalkyl radicals containing from 8 to 30 carbon atoms, such as from 10 to 24 carbon atoms, or from 12 to 18 carbon atoms.

Non-limiting examples of associative anionic polymers that may also be chosen include anionic polymers comprising at least one hydrophilic unit of olefinic unsaturated carboxylic acid type, and at least one hydrophobic unit exclusively of $(C_{10}-C_{30})$alkyl ester of unsaturated carboxylic acid type. Cationic associative polymers that may be chosen include, but are not limited to, quaternized cellulose derivatives and polyacrylates containing amine side groups.

Exemplary non-ionic associative polymers include celluloses modified with groups comprising at least one fatty chain, for instance hydroxyethyl celluloses modified with groups comprising at least one fatty chain, such as alkyl groups, e.g. $C_8-C_{22}$ alkyl groups, arylalkyl and alkylaryl groups, such as cetyl hydroxyethyl cellulose, also known as Natrosol® Plus (sold by the company Ashland); Bermocoll EHM 100 (sold by the company Berol Nobel), Amercell Polymer HM-1500® sold by Amerchol (hydroxyethylcellulose modified with a polyethylene glycol (15) nonylphenyl ether group, sold by the company Amerchol), celluloses modified with polyalkylene glycol alkylphenyl ether groups, guars such as hydroxypropyl guar, optionally modified with groups comprising at least one fatty chain such as an alkyl chain, for example JAGUAR® XC-95/3 (C14 alkyl chain, sold by the company Rhodia Chimie); Esaflor HM 22 (C22 alkyl chain, sold by the company Lamberti); RE210-18 (C14 alkyl chain) and RE205-1 (C20 alkyl chain, sold by the company Rhodia Chimie), copolymers of vinylpyrrolidone and of fatty-chain hydrophobic monomers, for instance Antaron® or Ganex® V216 (vinylpyrrolidone/hexadecene copolymers); Antaron® or Ganex® V220 (vinylpyrrolidone/eicosene copolymers), sold by the company I.S.P., copolymers of $C_1$-$C_6$ alkyl methacrylates or acrylates and of amphiphilic monomers comprising at least one fatty chain, and copolymers of hydrophilic methacrylates or acrylates and of hydrophobic monomers comprising at least one fatty chain, for instance the polyethylene glycol methacrylate/lauryl methacrylate copolymer; polymers with an aminoplast ether skeleton containing at least one fatty chain, such as the Pure Thix® nonionic associative water phase thickeners sold by the company Southern Clay Products, Inc.

Associative polyurethanes may also be chosen in various exemplary and non-limiting embodiments. These are nonionic block copolymers comprising in the chain both hydrophilic blocks usually of polyoxyethylene nature, and hydrophobic blocks that may be aliphatic sequences alone and/or cycloaliphatic and/or aromatic sequences. Associative polyurethanes comprise at least two hydrocarbon-based lipophilic chains containing from $C_6$ to $C_{30}$ carbon atoms, separated by a hydrophilic block, the hydrocarbon-based chains optionally being pendent chains or chains at the end of a hydrophilic block. For example, it is possible for one or more pendent chains to be provided. In addition, the polymer may comprise a hydrocarbon-based chain at one or both ends of a hydrophilic block. The associative polyurethanes may be arranged in triblock or multiblock form. The hydrophobic blocks may thus be at the each end of the chain (for example, triblock copolymer with a hydrophilic central block) or distributed both at the ends and within the chain (for example, multiblock copolymer). These polymers may also be graft polymers or starburst polymers. For example, the associative polyurethanes may be triblock copolymers in which the hydrophilic block is a polyoxyethylene chain containing from 50 to 1000 oxyethylene groups.

By way of non-limiting example, associative polymers of the polyurethane polyether type that may be used include the polymer $C_{16}$-$OE_{120}$-$C_{16}$ from Servo Delden (under the name SER AD FX1100), which is a molecule containing a urethane function and having a weight-average molecular weight of 1300), OE being an oxyethylene unit, Nuvis® FX 1100 (European and US INCI name "Steareth-100/PEG-136/HMDI Copolymer" sold by the company Elementis Specialties), and also Acrysol RM 184® (sold by the company Rohm and Haas); Elfacos® T210® (C12-C14 alkyl chain) and Elfacos® T212® (C18 alkyl chain) sold by the company Akzo. Further exemplary associative polymers that may be chosen include RHEOLATE® 205 containing a urea function, sold by Rheox, or RHEOLATE® 208 or 204, or RHEOLATE® FX1100 from Elementis. The product DW 1206B from Rohm & Haas containing a $C_{20}$ alkyl chain with a urethane bond, sold at a solids content of 20% in water, may also be used.

In yet further exemplary embodiments, solutions or dispersions of these polymers, especially in water or in aqueous-alcoholic medium, may be chosen. Examples of such polymers include SER AD FX1010, SER AD FX1035 and SER AD 1070 from Servo Delden, and RHEOLATE® 255, RHEOLATE® 278 and RHEOLATE® 244 sold by Rheox. Further examples include the products ACULYN™ 46, DW 1206F and DW 1206J, and also ACRYSOL RM 184 or ACRYSOL 44 from Rohm & Haas, and BORCHIGEL LW 44 from Borchers.

In at least one exemplary embodiment, the at least one thickening agent is chosen from copolymers resulting from the polymerization of at least one monomer (a) chosen from carboxylic acids possessing α,β-ethylenically unsaturated groups or their esters, with at least one monomer (b) possessing ethylenically unsaturated groups and comprising a hydrophobic group. Such copolymers may exhibit emulsifying properties.

As used herein, the term "copolymers" is intended to mean both copolymers obtained from two types of monomers and those obtained from more than two types of monomers, such as, for example, terpolymers obtained from three types of monomers. The chemical structure of the copolymers comprises at least one hydrophilic unit and at least one hydrophobic unit. The expression "hydrophobic unit" or "hydrophobic unit" is understood to mean a radical possessing a saturated or unsaturated and linear or branched hydrocarbon-based chain which comprises at least 8 carbon atoms, for example from 10 to 30 carbon atoms, as a further example from 12 to 30 carbon atoms, and as yet a further example from 18 to 30 carbon atoms.

In certain exemplary and non-limiting embodiments, the thickening copolymers are chosen from the copolymers resulting from the polymerization of:

(1) at least one monomer of formula (II):

wherein $R_1$ is chosen from H or $CH_3$ or $C_2H_5$, providing acrylic acid, methacrylic acid, or ethacrylic acid monomers, and (2) at least one monomer of ($C_{10}$-$C_{30}$)alkyl ester of unsaturated carboxylic acid type corresponding to the monomer of formula (III):

wherein $R_2$ is chosen from H or $CH_3$ or $C_2H_5$, providing acrylate, methacrylate or ethacrylate units, $R_3$ denoting a $C_{10}$-$C_{30}$ alkyl radical, such as a $C_{12}$-$C_{22}$ alkyl radical.

Non-limiting examples of ($C_{10}$-$C_{30}$)alkyl esters of unsaturated carboxylic acids are for example chosen from lauryl acrylate, stearyl acrylate, decyl acrylate, isodecyl acrylate, dodecyl acrylate and the corresponding methacrylates, such as lauryl methacrylate, stearyl methacrylate, decyl methacrylate, isodecyl methacrylate and dodecyl methacrylate, and mixtures thereof.

Additionally, crosslinked thickening polymers may be chosen according to further exemplary embodiments. For example, such polymers may be chosen from polymers resulting from the polymerization of a mixture of monomers comprising:

(1) acrylic acid, (2) an ester of formula (III) described above, in which $R_2$ is chosen from H or $CH_3$, $R_3$ denoting an alkyl radical having from 12 to 22 carbon atoms, and (3) a crosslinking agent, which is a well-known copolymerizable polyethylenic unsaturated monomer, such as diallyl phthalate, allyl (meth)acrylate, divinylbenzene, (poly)ethylene glycol dimethacrylate and methylenebisacrylamide.

For example, acrylate/$C_{10}$-$C_{30}$ alkyl acrylate copolymers (INCI name: Acrylates/C10-30 Alkyl Acrylate Crosspolymer), such as the products sold by Lubrizol under the trade names PEMULEN™ TR1, PEMULEN™ TR2, CARBOPOL® 1382 and CARBOPOL® EDT 2020 may be chosen.

In further embodiments, the at least one thickening agent may be chosen from nonionic homopolymers or copolymers containing ethylenically unsaturated monomers of the ester and/or amide type. For example, the products sold under the names CYANAMER P250 by the company CYTEC (polyacrylamide), methyl methacrylate/ethylene glycol dimethacrylate copolymers (such as PMMA MBX-8C by the company US COSMETICS), butyl methacrylate/methyl methacrylate copolymers (such as ACRYLOID B66 by the company RHOM HMS), and polymethyl methacrylates (BPA 500 by the company KOBO) may be chosen.

In yet further embodiments, the at least one thickening agent chosen from polymers of natural origin may include, for example, thickening polymers comprising at least one sugar unit, for instance nonionic guar gums, optionally modified with C1-C6 hydroxyalkyl groups; biopolysaccharide gums of microbial origin, such as scleroglucan gum (also known as *sclerotium* gum) or xanthan gum; gums derived from plant exudates, such as gum arabic, ghatti gum, karaya gum, gum tragacanth, carrageenan gum, agar gum and carob gum, *ceratonia siliqua* gum and *cyamopsis tetragonoloba* (guar) gum; pectins; alginates; starches; hydroxy(C1-C6)alkylcelluloses and carboxy(C1-C6)alkylcelluloses.

Non-limiting examples of nonionic, unmodified guar gums that may be used in various embodiments include Guargel D/15 (Noveon); Vidogum GH 175 (Unipectine), Meypro-Guar 50 and JAGUAR® C (Meyhall/Rhodia Chimie). Non-limiting examples of nonionic modified guar gums include Jaguar® HP8, HP60, HP120, DC 293 and HP 105 (Meyhall/Rhodia Chimie); and Galactasol 4H4FD2 (Ashland).

Further examples of useful thickening agents include scleroglucans, for example, Actigum™ CS from Sanofi Bio Industries; Amigel from Alban Muller International, and also the glyoxal-treated scleroglucans described in FR2633940); xanthan gums, for instance Keltrol®, Keltrol® T, Keltrol® Tf, Keltrol® Bt, Keltrol® Rd, Keltrol® Cg (Nutrasweet Kelco), Rhodicare® S and Rhodicare® H (Rhodia Chimie); starch derivatives, for instance Primogel® (Avebe); hydroxyethylcelluloses such as Cellosize® QP3L, QP4400H, QP30000H, HEC30000A and Polymer PCG10 (Amerchol), Natrosol™ 250HHR®, 250MR, 250M, 250HHXR, 250HHX, 250HR, HX (Hercules) and Tylose® H1000 (Hoechst); hydroxypropylcelluloses, for instance Klucel® EF, H, LHF, MF and G (Ashland); carboxymethylcelluloses, for instance Blanose® 7M8/SF, refined 7M, 7LF, 7MF, 9M31F, 12M31XP, 12M31P, 9M31XF, 7H, 7M31, 7H3SXF (Ashland), Aquasorb® A500 (Hercules), Ambergum® 1221 (Hercules), Cellogen® HP810A, HP6HS9 (Montello) and Primellose® (Avebe).

Exemplary modified nonionic guar gums may, for example, be modified with C1-C6 hydroxyalkyl groups. Exemplary hydroxyalkyl groups may include hydroxymethyl, hydroxyethyl, hydroxypropyl and hydroxybutyl groups.

Guar gums are well known in the state of the art and may, for example, be prepared by reacting the corresponding alkene oxides, such as for example propylene oxides, with guar gum so as to obtain a guar gum modified with hydroxypropyl groups. The hydroxyalkylation ratio, which corresponds to the number of alkylene oxide molecules consumed to the number of free hydroxyl functional groups present on the guar gum, may in at least certain exemplary embodiments vary from about 0.4 to about 1.2.

Exemplary and non-limiting nonionic guar gums, optionally modified with hydroxyalkyl groups, include those sold under the trade names JAGUAR® HP8, JAGUAR® HP60 and JAGUAR® HP120, JAGUAR® DC 293 and JAGUAR® HP 105 by the company RHODIA CHIMIE (RHODIA CHIMIE), and under the name GALACTASOL™ 4H4FD2 by the company ASHLAND.

Guar gums may also be modified with a quaternary ammonium group. Guar gums modified as such include Guar Hydroxypropyltrimonium Chloride, also known under the tradename JAGUAR® C-13S (RHODIA CHIMIE).

Exemplary and non-limiting celluloses include hydroxyethylcelluloses and hydroxypropylcelluloses. The products sold under the names KLUCEL EF, KLUCEL H, KLUCEL LHF, KLUCEL MF, KLUCEL G, by the company ASHLAND, CELLOSIZE POLYMER PCG-10 by the company AMERCHOL, may be chosen in various embodiments.

Exemplary, non-limiting thickening polysaccharides may be chosen from glucans, modified or unmodified starches (such as those derived, for example, from cereals such as wheat, corn or rice, vegetables such as golden pea, tubers such as potato or cassava), amylose, amylopectin, glycogen, dextrans, celluloses and derivatives thereof (methylcelluloses, hydroxyalkylcelluloses, ethylhydroxyethylcelluloses), mannans, xylans, lignins, arabans, galactans, galacturonans, chitin, chitosans, glucoronoxylans, arabinoxylans, xyloglucans, glucomannans, pectic acids and pectins, arabinogalactans, carrageenans, agars, gums arabic, gums tragacanth, Ghatti gums, Karaya gums, carob gums, galactomannans such as guar gums and their nonionic derivatives (hydroxypropylguar), and mixtures thereof.

Further, exemplary thickening agents include silicas, optionally hydrophobic; clays, such as montmorillonite, modified clays such as the bentones for example, stearalkonium hectorite, stearalkonium bentonite; polysaccharide alkyl ethers (optionally with the alkyl group having from 1 to 24 carbon atoms, for example from 1 to 10 carbon atoms, as a further example from 1 to 6 carbon atoms, and as yet a further example from 1 to 3 carbon atoms).

Thickening agents of the present disclosure may also include rheology modifiers. In accordance with the disclosure, rheology modifiers may, in various exemplary embodiments, be chosen from Polyacrylamide(and)C13-14 Isoparaffin(and)Laureth-7 (Sepigel™ 305 from Seppic), Hydroxypropyl Guar (JAGUAR® HP105 from Rhodia), *Cyamopsis Tetragonoloba* (Guar) Gum (Supercol U Guar Gum from Ashland), Acrylates/C10-30 Alkyl Acrylate Crosspolymer (Carbopol® Ultrez 20 Polymer from Lubrizol), Acrylates/C10-30 Alkyl Acrylate Crosspolymer (Permulen™ TR-1 from Lubrizol), Polyacrylate Crosspolymer-6 (Sepimax Zen from Seppic), *Sclerotium* Gum (Amigum from Alban Muller), Xanthan Gum(and)*Ceratonia Siliqua* Gum (Nomcort CG from Nisshin Oil Lio), Hydroxypropyl Guar (Jaguar® HP8 from Rhodia), Guar Hydroxypropyl Trimonium Chloride (Jaguar® C-13-S from Rhodia), Hydroxyethyl Cellulose (Natrosol® 250 MR from Ashland).

When anionic thickening agents are used, they are generally neutralized before being included in or as they are added to the compositions of the disclosure. Such anionic thickening agents may be neutralized by employing traditional neutralizing agents such as alkanolamines, for example, monoethanolamine and diethanolamine; aminomethyl propanol; basic amino acids, for example arginine and lysine; and ammonium compounds and their salts.

Cationic thickening agents of the disclosure may also be chosen from non-associative cationic polymers such as dimethylaminoethyl methacrylate homopolymers quaternized with methyl chloride or dimethylaminoethyl methacrylate copolymers quaternized with methyl chloride and acrylamide. Among the homopolymers of this type, mention may be made of methacryloylethyl trimethyl ammonium chloride homopolymer, INCI name: polyquaternium-37).

Another suitable example of a cationic thickening agent is a product known by the INCI name of polyacrylate-1 crosspolymer (Carbopol® Aqua CC, from the company, Lubrizol).

It is contemplated that, in at least certain exemplary and non-limiting embodiments, the thickening agents of the disclosure may include compounds such as gellifying and viscosity modifying agents. For example, compositions of the disclosure may employ at least one water-soluble resin such as polyethylene oxide having a molecular weight ranging from 100,000 to 10,000,000. Examples of such polyethylene oxides include, but not limited to, Polyox water-soluble resins manufactured by Dow under the INCI names of PEG-2M, PEG-5M, PEG-7M, PEG-14M, PEG-23M, PEG-45M, PEG-90M, PEG-160M, and PEG-180M. PEG-90M is known under the tradename of Polyox™ WSR 301, and PEG-45M is known under the tradename Polyox™ WSR 60k.

The amounts of thickening agents in the compositions of the disclosure may range from about 0.1% to about 20% by weight, or such as from about 0.5% to about 15% by weight, or such as from about 0.5% to about 10% by weight, or such as from about 1% to about 5% by weight, relative to the total weight of the composition.

Water

The compositions of the present invention contain water. Water can be present in the amount of about 95%, 92%, 90%, 89%, 88%, 87%, 85%, 84%, 83%, 82%, 80%, 70%, 60%, 50%, 40%, 30%, 20%, 10%, 5% by weight or less, relative the total weight of the compositions. Additionally, water can be present in the compositions of the present invention in the amount of from about 20% to about 95% by weight, or from about 50% to about 90% by weight, or from about 60% to about 88% by weight, relative to the weight of the compositions.

In other embodiments, water can be present in the compositions of the present invention in the amount of at least about 95%, 92%, 90%, 89%, 88%, 87%, 85%, 84%, 83%, 82%, 80%, 70%, 60%, 50%, 40%, 30%, 20%, 10%, 5% by weight or less, based on the total weight of the compositions.

Cosmetically Acceptable Solvent

The compositions of the present invention may further comprise at least one cosmetically acceptable solvent comprising organic solvents chosen from volatile and nonvolatile organic solvents.

Suitable organic solvents are typically C2-C8 alcohols, glycols, polyols, polyol ethers, glycol ethers, glycerin, hydrocarbons, oils, and mixtures thereof. Examples of organic solvents include, but are not limited to, ethanol, isopropyl alcohol, benzyl alcohol, phenyl ethyl alcohol, propylene glycol, pentylene glycol, hexylene glycol, glycerol, and mixtures thereof.

Other suitable organic solvents include glycol ethers, for example, ethylene glycol and its ethers such as ethylene glycol monomethyl ether, ethylene glycol monopropyl ether, ethylene glycol monobutyl ether, propylene glycol and its ethers, such as propylene glycol monomethyl ether, propylene glycol monopropyl ether, propylene glycol monobutyl ether, dipropylene glycol and diethylene glycol alkyl ethers, such as diethylene glycol monoethyl ether, diethylene glycolmonobutyl ether, and dipropylene glycol n-butyl ether. Glycol ethers are commercially available from The Dow Chemical Company under the DOW E-series and DOW P-series. One preferred glycol ether for use in the present invention is dipropylene glycol n-butyl ether, known under the tradename of DOWANOL™ DPnB.

Suitable organic solvents also include synthetic oils and hydrocarbon oils include mineral oil, petrolatum, and $C_{10}$-$C_{40}$ hydrocarbons which may be aliphatic (with a straight, branched or cyclic chain), aromatic, arylaliphatic such as paraffins, iso-paraffins, isododecanes, aromatic hydrocarbons, polybutene, hydrogenated polyisobutene, hydrogenated polydecene, polydecene, squalene, petrolatum and isoparaffins, silicone oils, fluoro oils and mixtures, thereof.

The term "hydrocarbon-based oil" or "hydrocarbon oil" refers to oil mainly containing hydrogen and carbon atoms and possibly oxygen, nitrogen, sulfur and/or phosphorus atoms. Representative examples of hydrocarbon-based oils include oils containing from 8 to 16 carbon atoms, and especially branched C8-C16 alkanes (also known as isoparaffins), for instance isododecane (also known as 2,2,4,4,6-pentamethylheptane), isodecane and isohexadecane.

Examples of silicone oils that may be useful in the present invention include nonvolatile silicone oils such as polydimethylsiloxanes (PDMS), polydimethylsiloxanes comprising alkyl or alkoxy groups that are pendent and/or at the end of a silicone chain, these groups each containing from 2 to 24 carbon atoms, phenyl silicones, for instance phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates, and dimethicones or phenyltrimethicones with a viscosity of less than or equal to 100 cSt.

Other representative examples of silicone oils that may be useful in the present invention include volatile silicone oils such as linear or cyclic silicone oils, especially those with a viscosity ÿ centistokes (8×10-6 m 2/s) and especially containing from 2 to 10 silicon atoms and in particular from 2 to 7 silicon atoms, these silicones optionally comprising alkyl or alkoxy groups containing from 1 to 10 carbon atoms. Specific examples include dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Representative examples of fluoro oils that may be suitable for use in the present invention include volatile fluro oils such as nonafluoromethoxybutane and perfluoro-methylcyclopentane.

The amount of the organic solvent/compound present in the compositions of the present invention can range from about 0.5% to about 60%, or from about 0.5% to about 40%, or from about 0.5% to about 30%, or from about 0.5% to about 20%, and in some embodiments, from about 0.5% to about 15%, by weight, or preferably from about 1% to about 10%, by weight, or more preferably from about 1.5% to about 8%, by weight, or from about 2% to about 6%, by weight, including all ranges and subranges there-between, relative to the total weight of the composition.

In some embodiments, the amount of the organic solvent/compound present in the compositions of the present invention is at about 2%, about 2.5%, about 3%, about 3.5%, about 4%, about 4.5%, about 5%, about 5.5% or about 6% by weight, including all ranges and subranges there-between, relative to the total weight of the composition.

In certain embodiments, compositions of the present invention comprise both water and organic solvents/compounds selected from volatile organic solvents, non-volatile organic solvents, and mixtures thereof.

Preferred examples of organic solvents/compounds include volatile organic solvents such as C2 to C4 monoalcohols, such as ethanol, isopropyl alcohol, butanol, polyols such as C2-C6 glycols e.g., propylene glycol, butylene glycol, pentylene glycol, hexylene glycol, glycerol, isododecane, volatile polyol ethers, volatile glycol ethers, acetone, propylene carbonate, benzyl alcohol, and mixtures thereof. In certain embodiments, it is preferred that the amount of volatile organic solvent/compound does not exceed 55% by weight, relative to the weight of the composition of the present invention.

In other certain embodiments, it is preferred that the amount of volatile organic solvent/compound does not exceed 20% by weight, relative to the weight of the composition of the present invention.

In yet other certain embodiments, it is preferred that the amount of volatile organic solvent/compound does not exceed 10% by weight, relative to the weight of the composition of the present invention.

In preferred embodiments, the amount of volatile organic solvent/compound does not exceed 6% by weight, relative to the weight of the composition of the present invention.

Other preferred examples of organic solvents/compounds include nonvolatile organic solvents such as hydrocarbons such as straight chain hydrocarbons, nonvolatile silicone oils, mineral oil, polybutene, hydrogenated polyisobutene, hydrogenated polydecene, polydecene, squalene, petrolatum, isoparaffins, nonvolatile glycol ethers, and mixtures, thereof.

In certain embodiments, it is preferred that the amount of nonvolatile organic solvent/compound does not exceed 40% by weight, or does not exceed 20% by weight, or does not exceed 10% by weight, relative to the weight of the composition of the present invention.

In certain embodiments of the present invention, the at least one organic solvent is chosen from ethanol.

Intermediate Agent

The intermediate agent of the present invention may be any shampoo or conditioner composition. Preferably, the intermediate agent has a neutral pH.

Auxiliary Ingredients

The compositions according to the invention may further comprise any auxiliary ingredient usually used in the field under consideration, selected, for example, from conditioning agents, natural and synthetic oils, humectants, shine agents, fillers, colorants, pigments, chelating agents, sequestering agents, fragrances, preservatives, stabilizers, and mixtures thereof.

It is a matter of routine operations for a person skilled in the art to adjust the nature and amount of the additives present in the compositions in accordance with the invention such that the desired cosmetic properties and stability properties thereof are not thereby affected.

pH

In certain embodiments, the neutralizing agent is used in an amount such that the pH of the compositions of the invention is from about pH 2 to less than about 7, such as from about pH 2.5 to about 6.5, or preferably from about pH 3 to about 6, or more preferably from about pH 3 to about 5, or even more preferably from about pH 3 to about 4, including all ranges and subranges there-between.

In some embodiments, the neutralizing agent is used in an amount such that the pH of the compositions of the invention is from about 2 to 6, including all ranges and subranges there-between.

In other embodiments, the neutralizing agent is used in an amount such that the pH of the compositions of the invention is from about 2 to 4, including all ranges and subranges there-between.

In certain other embodiments, the pH of the compositions of the invention is about 2, 2.5, 3, 3.5, 4, 4.5, 5, 5.5, 6, 6.5.

pH can be adjusted with acidic agents other than the thiol-based reducing agents of the invention such as mineral acids, chlorhydric acid or phosphoric acid, or with basic agents such as mineral basic agents as ammonia, carbonates, bicarbonates, hydroxides or organic basic agents such as alcanolamines.

All numbers expressing pH values are to be understood as being modified in all instances by the term "about" which encompasses up to +/−0.2. For example, a pH value of about 7.0 refers to 7+/−0.2.

The compositions of the present invention are preferably in the form of an emulsion, for example, oil-in-water emulsion and water-in-oil emulsion.

In other embodiments, the composition of the present invention has a viscosity of from about 60 M2 to about 70 M2, preferably from about 62 M2 to about 68 M2, more preferably from about 62 M2 to about 65 M2, including all ranges and subranges therebetween, as measured by a Rhéomat RM180 at 25° C.

In certain preferred embodiments, the composition of the present invention has a viscosity of from about 62 M2 to about 65 M2 and a pH ranging from about pH 2 to about 6.

In some preferred embodiments, the composition of the present invention has a viscosity of from about 62 M2 to about 65 M2 and a pH ranging from about 2 to about 4.

All numbers expressing viscosity values are to be understood as being modified in all instances by the term "about" which encompasses up to +/−0.2. For example, a viscosity value of about 64.2 M2 refers to 64.2+/−0.2 M2.

In preferred embodiments, the composition of the present invention is a hair straightening composition.

The composition of the present invention is stable such that the straightening efficacy of the composition is preserved until the composition is ready to be used. In addition, the compositions of the present invention did not exhibit phase separation.

Methods of Making

The compositions of the present invention are made by combining at least one reducing agent, at least one neutralizing agent, at least two fatty substances, at least one alkoylated fatty alcohol, optionally at least one quaternary ammonium compound, and water.

In one embodiment, the method of making the compositions of the present invention comprises the steps of:

(1) combining:
(a) at least one thiol-based compound chosen from thiolactic acid, thiolactic acid derivatives, their salts, and mixtures thereof;
(b) at least one neutralizing agent; and
(c) water;
all weights being based on the total weight of the composition; and
(2) mixing (a) to (c) in order to form a composition having a pH ranging from about 2 to less than 7.

In one embodiment, the invention also concerns a process of shaping or altering the shape or caring of hair. The process comprises the steps of:

(1) applying onto the hair, a composition containing:
(a) at least one thiol-based compound chosen from thiolactic acid, thiolactic acid derivatives, their salts, and mixtures thereof;
(b) at least one neutralizing agent, preferably selected from aminomethyl propanol, monoethanolamine, sodium hydroxide, and mixtures thereof;
(c) at least two fatty substances comprising:
  i. from about 1% to about 60% by weight of a first fatty substance selected from alkanes, esters of fatty acid, esters of fatty alcohol, hydrocarbons, silicones, non-silicone waxes, mineral oils, vegetable oils, non-silicone synthetic oils, and mixtures thereof; and
  ii. from about 5% to about 10% by weight of a second fatty substance selected from fatty alcohols;
(d) from about 2.5% to about 6% by weight of at least one alkyl(ether)phosphate selected from PPG-5-Ceteth-10 phosphate, Oleth-3 phosphate, Oleth-10 phosphate, Ceteth-10 phosphate, a mixture of Ceteth-10 phosphate and Dicetyl phosphate, Dicetyl phosphate, Cetyl phosphate, Stearyl phosphate and mixtures thereof; and
(e) water;
all weights being based on the total weight of the composition;
wherein the pH of the composition ranges from about 2 to less than 7.
(2) brushing or combing or smoothing the hair;
(3) heating the hair at a temperature of at least 40° C., preferably at a temperature of from about 40° C. to about 250° C., or from about 50° C. to about 250° C. or from about 60° C. to about 230° C. or from about 60° C. to about 210° C. or from about 70° C. to about 200° C. or from about 70° C. to about 190° C., including all ranges and subranges therebetween; while optionally applying a smoothing action on the hair, wherein when a smoothing action is employed, the heating action and smoothing action are accomplished by use of a heating device such as a flat iron; and
(4) rinsing the hair with water or contacting the hair with an intermediate agent, followed by rinsing with water.

Preferably, before the composition in the process above is applied onto the hair, the hair is first contacted with a shampoo and/or conditioner and then rinsed with water.

In certain embodiments, the intermediate agent in the process above is a shampoo or conditioner, preferably having a neutral pH.

In certain embodiments, the hair treated and processed according to the invention is contacted with a neutralizing composition containing at least one oxidizing agent. In some embodiments, the at least one oxidizing agent can be selected from hydrogen peroxide, persalts such as persulphates, percarbonates, and perborates, urea peroxide, alkaline bromates, and polythionates. In some embodiments, hydrogen peroxide is used.

In some embodiments, the at least one oxidizing agent may be present in an amount ranging from 0.1 to 50 percent by weight, such as from 1 to 20 percent by weight, relative to the total weight of the composition.

In some embodiments, when the at least one oxidizing agent is hydrogen peroxide, the composition described herein may comprise at least one agent that stabilizes hydrogen peroxide. As examples of agents that stabilize hydrogen peroxide, non-limiting mention may be made of the pyrophosphates of the alkali or alkaline-earth metals, the stannates of the alkali or alkaline-earth metals, and phenacetin or the salts of acids and of oxyquinoline, such as oxyquinoline sulphate. In some embodiments, the at least one agent that stabilizes hydrogen peroxide may be present in an amount ranging from 0.0001 to 5 percent by weight, such as from 0.01 to 2 percent by weight, relative to the total weight of the composition In certain embodiments, the composition is allowed to remain (leave-on time) on the keratin fibers for a pre-determined amount of time, for example, from about 1 to about 60 minutes, or such as from about 1 to about 45 minutes, or such as from about 1 to about 30 minutes, or such as from about 5 to about 30 minutes, or such as at about 30 minutes, or such as at about 20 minutes, or such as at about 10 minutes. The pre-determined amount of time is sufficient to achieve satisfactory straightening or shaping or altering the shape of the keratin fibers such as hair on the human head.

In other embodiments, the composition is rinsed from the hair with water before brushing the hair. The rinsed hair may also be subjected to a detangling or smoothing action before brushing the hair.

Suitable devices for detangling or brushing or smoothing the hair include a hair brush, comb, or heating flat iron. The smoothing or detangling action on the hair may also include running the fingers through the hair.

The composition can also be applied onto the hair using an applicator device or with the hands or gloved hands.

A suitable applicator device is an applicator brush or applicator comb or applicator spatula or a dispenser or applicator tip attached to the container holding the composition.

Heat (at a temperature of at least 40° C.) can be applied to the hair while the smoothing action is performed on the hair. The heat source can be chosen from a blow dryer, a flat iron, a hair dryer, a heat lamp, a heat wand, or other similar devices.

In addition, independently of the embodiment use, the composition present on the fibers or hair is left in place for a time, generally, from about 1 minute to about 60 minutes, such as from about 1 minute to about 45 minutes, or such as from about 1 minute to about 30 minutes, or such as from about 5 minutes to about 30 minutes, or such as at about 30 minutes, or such as of about 20 minutes or such as of about 10 minutes.

It has surprisingly and unexpectedly discovered that the application of the composition onto the fibers results in satisfactory straightening of hair.

The straightening effects obtained using the compositions and process of the present disclosure may also be durable or wash resistant.

The degree of straightening or frizz control or volume reduction of the hair may be evaluated by visually assessing the reduction in curliness and/or waviness and/or frizziness and/or volume (spread or area occupied) of the hair after contacting the hair with the composition of the invention. Another type of evaluation for degree of straightening or volume reduction can also involve measuring the length of the hair as well as the width of the bulk of hair before and after contacting the hair with the composition.

It was surprisingly and unexpectedly discovered that the hair contacted with the compositions of the invention did not feel as rough and visually appeared to be more smooth, extended and straight compared to hair contacted with conventional or traditional straightening compositions.

The process of the present disclosure can impart to hair one or more of: straightening effects; manageability; frizz control; volume reduction or volume control; styling effects; curling effects; texlaxing effects; improvement or retention of curl definition; humidity resistance; or improvement of the appearance of hair.

The compositions of the present invention may be packaged in any suitable container such as a tube, a jar or a bottle, a squeeze tube or squeeze bottle. Additionally, an applicator device can be attached or connected to the opening of the packaging/squeeze tube or bottle wherein the applicator device is a brush or a comb with teeth such that the ends of the teeth have openings from which the composition of the invention can flow through and be applied directly onto the hair.

The composition of the present invention may also be provided as component of a kit for shaping or altering the shape of hair wherein the kit can additionally contain other components such as an intermediate agent having a neutral pH chosen from a shampoo or a conditioner.

As used herein, the process and composition disclosed herein may be used on the hair that has not been artificially dyed, pigmented or permed.

As used herein, the process and composition disclosed herein may be also used on the hair that has been artificially dyed, pigmented or permed.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result.

EXAMPLES

The following Examples are intended to be non-restrictive and explanatory only, with the scope of the invention being defined by the claims.

The ingredient amounts in the compositions/formulas described below are expressed in % by weight, based on the total weight of the composition/formula.

Example 1

A. Processes for Treating and Shaping or Altering the Shape of Hair (e.g., Straightening) and Assessments of Performance These studies were conducted on curly or wavy hair swatches (virgin hair, i.e., not chemically treated) using the compositions of the invention (exemplified below). The process of treating and shaping or altering the shape of hair or caring for the hair was performed according to a rinsing protocol (Process 1) and a non-rinsing protocol (Process 2).

For Process 1, the following steps were followed:
1. the hair was contacted with a shampoo (neutral pH);
2. the hair was rinsed with water and optionally, blow dried;
3. the inventive composition was applied onto the hair using an applicator brush device (approximately 1 gram of the composition per gram of hair or approximately 300 grams per head of hair);
4. the inventive composition was allowed to remain on the hair for thirty minutes;
5. the inventive composition was rinsed off the hair;
6. the hair was brushed with a hair brush using 20 to 30 strokes;
7. the hair was smoothed and heated with a flat iron set at 230° C. and using 10 strokes (or passes);
8. the hair was contacted with a shampoo and/or a conditioner (neutral pH);
9. the hair was rinsed with water (if shampoo is used in step 7, then this rinsing step can optionally, be followed by a step of contacting the hair with a conditioner (neutral pH), and then rinsing with water);
10. the shampoo/rinse/optional conditioning/rinse cycle was repeated as many times as desired.

For Process 2, the following steps were followed:
1. the hair was contacted with a shampoo (neutral pH);
2. the hair was rinsed with water and optionally, blow dried;
3. the inventive composition was applied onto the hair using an applicator brush device (approximately 1 gram of the composition per gram of hair or approximately 300 grams per head of hair);
4. the inventive composition was allowed to remain on the hair for thirty minutes;
5. the hair was brushed with a hair brush using 20 to 30 strokes;
6. the hair was smoothed and heated with a flat iron set at 230° C. and using 10 strokes (or passes);
7. the hair was contacted with a shampoo and/or a conditioner (neutral pH);
8. the hair was rinsed with water; (if shampoo is used in step 7, then this rinsing step can optionally, be followed by a step of contacting the hair with a conditioner (neutral pH), and then rinsing with water);
9. the shampoo/rinse/optional conditioning/rinse cycle was repeated as many times as desired.

Example 1

B. Method of Assessment of Performance Such as Straightening, Reduction of Frizziness and Volume of Hair Hair swatches were visually assessed for the following attributes: reduction of the volume (width) of the hair (also indicative of the degree of frizziness of and degree of discipline of the hair) and degree of straightening or smoothing of the hair swatch. These attributes can also be measured or assessed on a 1 to 4 scale, with 4 being the smallest volume which indicates the greatest degree of smoothing or straightening or lengthening of the hair, greatest reduction in frizziness or volume of the hair and greatest amount of discipline of the hair.

Example 2

Compositions

TABLE 1

Aqueous Compositions
Formulas with different concentrations of Thiolactic acid in aqueous solutions having similar pH values:

|  | Formula 1 | Formula 2 | Formula 3 |
|---|---|---|---|
| pH value | 3.51 | 3.54 | 3.51 |
| % by weight thiolactic acid | 4 | 6 | 8 |
| % by wt of sodium hydroxide | to pH | to pH | to pH |
| Straightening performance | 3.0 | 3.5 | 4.0 |

Swatch evaluation was performed on curly or wavy hair swatches (virgin hair, i.e., not chemically treated) in accordance with the assessment method in Example 1B above. From the table above, it was found that at similar pH values, the degree of straightening increased as the level of thiolactic acid increased.

TABLE 2

Gel Composition

| INCI US | Formula A, % by weight |
|---|---|
| AMINOMETHYL PROPANOL | 2 |
| THIOLACTIC ACID | 8 |
| HYDROXYETHYLCELLULOSE | 0.75 |
| CELLULOSE PCG-10 (AMERCHOL/DOW CHEMICAL) | |
| PEG-12 DIMETHICONE | 2 |
| WATER | Q.S. to 100 |

TABLE 3

Gel Compositions

| INCI US | Formula B, % by weight pH = 3.51 | Formula C, % by weight pH = 3.54 | Formula D, % by weight pH = 3.51 | Formula E, % by weight pH = 3.51 |
|---|---|---|---|---|
| AMINOMETHYL PROPANOL | 3 | 3 | 3 | 3 |
| THIOLACTIC ACID | 8 | 8 | 8 | 8 |
| HYDROXYETHYLCELLULOSE CELLOSIZE HYDROXYETHYL CELLULOSE PCG-10 (AMERCHOL/DOW CHEMICAL) | 0.75 | 0.75 | 0.75 | 0.75 |
| DIMETHICONE, 80% (and) AMODIMETHICONE, 20% KF 8020 (SHIN ET SU) | 2 | — | — | — |
| DIMETHICONE | — | 2 | — | — |
| AMODIMETHICONE IN EMULSION (57.5% ACTIVE) | — | — | 2 | — |
| CYCLOPENTASILOXANE (85.3% BY WEIGHT) DIMETHICONOL (14.7% BY WEIGHT) | — | — | — | 2 |
| WATER | QS 100 | QS 100 | QS 100 | QS 100 |

The gel compositions above were each prepared according to the general procedure:
2. Heat water to about 70° C.
3. Add the cellulose material and keep the temperature at about 70° C. and agitate the mixture for 30 minutes.
4. Add the silicone material and mix for another 15 minutes at 70° C.
5. Cool to 25° C.
6. Add the neutralizing agent at 25° C. with agitation and then add the thiolactic acid.
7. Adjust the pH and check the viscosity.

The viscosity of the inventive composition was measured using the Mettler RM 180 Rheomat, viscometer spindle #2, at 25° C. (uD=Units of Deflection).

A viscosity measurement in M2 units ranging up from about 60 to 65 M2 corresponded to a texture and consistency of a gel composition. The gel texture provided the benefits of ease of application of the composition into the hair, spreadability of the composition on the hair, and/or ease of brushing or combing the hair. The gel compositions did not readily drip off the hair contacted with the compositions and remained on the hair during the straightening processing time.

TABLE 4

Emulsion Composition

| INCI US | Formula F, % by weight |
|---|---|
| ETHANOLAMINE | 3 |
| THIOLACTIC ACID | 8 |
| POLYQUATERNIUM-6 | 1 |
| POLYQUATERNIUM-67 | 0.1896 |
| PPG-5-CETETH-20 | 3 |
| MINERAL OIL | 43.1 |
| AMODIMETHICONE | 1.15 |
| CETETH-10 PHOSPHATE | 1.75 |
| CETEARYL ALCOHOL | 8.25 |
| WATER | Q.S. to 100 |

TABLE 5

Emulsion Composition

| INCI US | Formula G, % by weight |
|---|---|
| AMINOMETHYL PROPANOL | 3 |
| THIOLACTIC ACID | 8 |

TABLE 5-continued

Emulsion Composition

| INCI US | Formula G, % by weight |
|---|---|
| POLYQUATERNIUM-6 | 1 |
| PPG-5-CETETH-20 | 2.1 |
| MINERAL OIL | 2.1 |
| CETETH-10 PHOSPHATE | 0.875 |
| CETEARYL ALCOHOL | 7.525 |
| WATER | Q.S. to 100 |

The emulsion compositions above were each prepared according to the general procedure:

1. Heat water to about 60° C.
2. Add the PPG-5-ceteth-20 and keep the temperature at about 60° C. and agitate the mixture for 10 minutes.
3. Combine Ceteth-10 Phosphate, Cetearyl alcohol, Polyquaternium-67 (if present), and Mineral Oil and mix for another 25 minutes at 60° C. and add to PPG-5 cetheth-20 and water mixture.
4. If present, stir Polyquaternium-6 for 10 minutes at 40° C. and add to resulting mixture.
5. Combine the neutralizing agent at 25° C. with agitation and then add the thiolactic acid.
6. Adjust the pH and check the viscosity.

The viscosity of the inventive composition was measured using the Mettler RM 180 Rheomat, at 25° C. (uD=Units of Deflection).

Viscosity measurements corresponded to a texture and consistency of an emulsion or cream composition. The cream texture provided the benefits of ease of application of the composition into the hair, spreadability of the composition on the hair, and/or ease of brushing or combing the hair. The emulsion composition with the cream texture also did not readily drip off the hair contacted with the composition and remained on the hair during the straightening processing time.

The consistency and texture of the inventive formulas above (aqueous, gel and emulsion) allow for the formulas to be packaged in various ways, such as in jars, in tubes (e.g., squeeze tubes) or in bottles (eg, applicator bottles).

The formulas above were also found to be stable. Stability was measured by placing the formulas in a humidity-controlled environment set at 4° C., 25° C. and 45° C. for at least 2 months. The formula was considered to be stable when no phase separation is observed and there were very little fluctuations in viscosity and pH.

Example 3

Assessments of Performance and Straightening or Smoothing, Reduction of Frizziness and Volume of Hair The performance of the compositions in Example 2 on hair was assessed according to the assessment method described in Example 1 B.

Assessments were performed on hair swatches before treating the swatch with the gel composition, formula A, after treating a swatch with formula A by subjecting the swatch to the above-described rinsing protocol (process 1), and after treating a swatch with formula A by subjecting the swatch to the above-described non-rinsing protocol (process 2), It was found that the gel formula A significantly straightened the hair from a curly state, imparted excellent discipline to the hair (i.e., very low amount of or no frizz) and significantly reduced the volume of the hair.

For formulas B to E, it was observed that the degree of straightening and/or discipline and/or volume reduction was comparable to formula A. However, the hair treated with formula A had better or increased natural feel to the touch.

It was also found that the use of hydroxyethylcellulose in the gel formulas improved the quality and process of straightening the hair, i.e, it was easier to brush the hair and the flat iron plates slid/passed better or easier over the hair.

The FIG. shows images of hair swatches before treating the swatch with the emulsion composition, formula G, after treating a swatch with formula G by subjecting the swatch to the above-described rinsing protocol (process 1), and after treating a swatch with formula G by subjecting the swatch to the above-described non-rinsing protocol (process 2), It was found that the emulsion formula significantly straightened the hair from a curly state, imparted excellent discipline to the hair (i.e., very low amount of or no frizz) and significantly reduced the volume of the hair.

The hair swatch subjected with formula G and the rinsing protocol (process 1) had a measurement of 4, which indicated the greatest degree of straightening and reduction of frizziness to the hair. The hair swatch subjected with formula G and the non-rinsing protocol (process 2) had a measurement of 3, which also showed a significant degree of straightness and reduction of frizziness in comparison to the hair swatch before treatment.

Example 4

Testing Various Ingredients Employed in the Formula

A. Testing different neutralizing agents (sodium hydroxide and aminomethyl propanol) in aqueous solutions containing 8% by weight thiolactic acid at different pH values on curly or wavy hair swatches (virgin hair, i.e., not chemically treated) using Process 1.

TABLE 6

| Sodium Hydroxide | | | | | | |
|---|---|---|---|---|---|---|
| pH value | 2 | 4 | 6 | 8 | 10 | 12 |
| % by wt of sodium hydroxide | 0.2 | 2.0 | 3.0 | 3.8 | 4.4 | 6.3 |
| Straightening performance | 3.5 | 3.5 | 3.5 | 2.0 | — | — |

At pH values of 8 to 12, a high level of sensitization was observed; hair breakage was also observed in this pH range. As such, the hair was not rated for straightening performance at pH values of 10 and 12. At pH values of 2 to 6, hair cosmeticity and discipline was improved.

TABLE 7

| Aminomethyl Propanol | | | | | | |
|---|---|---|---|---|---|---|
| pH value | 2 | 4 | 6 | 8 | 10 | 12 |
| % by wt of Aminomethyl Propanol | 0.3 | 4.6 | 6.5 | 7.0 | 15.8 | 30.0 |
| Straightening performance | 3.5 | 3.5 | 1.5 | 2.5 | — | — |

At pH values of 6 to 12, a high level of sensitization was observed; hair breakage was also observed in this pH range. The hair was not rated for straightening performance at pH values of 10 and 12. At pH values of 2 to 4, hair cosmeticity and discipline was improved; the hair also felt natural to the touch.

B. Swatch evaluation using two different cellulose compounds as viscosity/thickening agent in aqueous on curly or wavy hair swatches (virgin hair, i.e., not chemically treated).

TABLE 8

| | Viscosity/Thickening agent | |
|---|---|---|
| INCI US | Formula 4 % by weight | Formula 5 % by weight |
| SODIUM HYDROXIDE | 1 | 1 |
| THIOLACTIC ACID | 8 | 8 |
| HYDROXYETHYLCELLULOSE | 0.75 | — |
| METHYL HYDROXYETHYLCELLULOSE (90% active) | — | 0.75 |
| WATER | 90.25 | 90.25 |

Both formulas above provided a more natural touch to the hair. Hydroxyethylcellulose. In addition, Formula 4 had better viscosity and the hair treated with this formula was easier to brush.

D: Swatch evaluation using different amounts of hydroxyethylcellulose in aqueous solutions on curly or wavy hair swatches (virgin hair, i.e., not chemically treated), Three aqueous solutions containing water, 8% by weight thiolactic acid, 3% by weight aminomethyl propanol, 2% by weight of silicone material comprising dimethicone and amodimethicone (KF 8020) and hydroxyethylcellulose at 0.75%, 1%, and 1.25% by weight were tested on hair swatches (all weights based on the total weight of the solutions).

The degrees of volume reduction and discipline (reduced or no frizz) observed on the treated swatches treated with compositions having from 0.75 to 1.25% by weight of hydroxyethylcellulose were comparable to each other.

It is to be understood that the foregoing describes preferred embodiments of the invention and that modifications may be made therein without departing from the spirit or scope of the invention as set forth in the claims.

The invention claimed is:

1. A hair cosmetic composition comprising:
   (a) from 1% to 15% by weight of at least one thiol-based compound selected from thiolactic acid, thiolactic acid derivatives, their salts, and mixtures thereof;
   (b) at least one neutralizing agent in an amount such that the pH of the composition ranges from 2 to 6, wherein the at least one neutralizing agent is selected from organic amines, alkali metal hydroxides, alkali earth metal hydroxides, alkali metal carbonates, alkali metal phosphates, and mixtures thereof;
   (c) from 0.1% to 20% by weight of at least one thickening agent selected from celluloses and their derivatives, nonionic guar gums, biopolysaccharide gums of microbial origin, scleroglucan gum, xanthan gum, gums derived from plant exudates, gum arabic, ghatti gum, karaya gum, gum tragacanth, carrageenan gum, agar gum, carob gum, pectins, alginates, starches, and mixtures thereof;
   (d) water; and
   (e) from 0.5% to 8% by weight of at least one silicone compound;
      wherein all weights are based on the total weight of the composition; and the composition is free of pyridine and derivatives thereof.

2. The composition, according to claim 1, wherein the at least one active agent is thiolactic acid.

3. The composition, according to claim 1, wherein the at least neutralizing agent is aminomethyl propanol and is present in an amount of from 0.1% to 6.3% by weight based on the total weight of the composition.

4. The composition, according to claim 1, wherein the at least neutralizing agent is sodium hydroxide and is present in an amount of from 0.1% to 4.1% by weight, based on the total weight of the composition.

5. The composition, according to claim 1, wherein the at least neutralizing agent is monoethanolamine and is present in an amount of from 0.1% to 4.1% by weight, based on the total weight of the composition.

6. The composition, according to claim 1, further comprising at least one fatty substance selected from the group consisting of alkanes, esters of fatty acid, esters of fatty alcohol, hydrocarbons, silicones, non-silicone waxes, mineral oil, vegetable oils, non-silicone synthetic oils, fatty alcohols and mixtures thereof.

7. The composition, according to claim 6, wherein the at least one fatty substance is present in an amount of from 1% to 80% by weight based on the total weight of the composition.

8. The composition, according to claim 1, further comprising at least one nonionic surfactant selected from the group consisting of alkoxylated fatty alcohols, alkyl(ether) phosphates, alkylpolyglucosides, and mixtures thereof and present in an amount of from 0.1% to 20% by weight, based on the total weight of the composition.

9. The composition according to claim 8, wherein the at least one nonionic surfactant is selected from the group consisting of PPG-5-Ceteth-10 phosphate, Oleth-3 phosphate, Oleth-10 phosphate, Ceteth-10 phosphate, a mixture of Ceteth-10 phosphate and Dicetyl phosphate, Dicetyl phosphate, Cetyl phosphate, Stearyl phosphate and mixtures thereof.

10. The composition according to claim 1, further comprising at least one quaternary ammonium compound present in an amount of from 0.5% to 5% by weight, based on the total weight of the composition.

11. The composition according to claim 10, wherein the at least one quaternary ammonium compound is selected from the group consisting of behentrimoinium chloride, cetrimonium chloride, behentrimonium methosulfate, quaternium-87, quaternium-83, polyquaternium compounds, and mixtures thereof.

12. The composition of claim 1, wherein the pH of the composition ranges from 3 to 5.

13. The composition of claim 1, wherein the pH of the composition ranges from 2 to 4.

14. A hair cosmetic composition comprising:
   (a) 1% to 15% by weight of at least one thiol-based compound selected from thiolactic acid, thiolactic acid derivatives, their salts, and mixtures thereof;
   (b) at least one neutralizing agent in an amount such that the pH of the composition ranges from 2 to 6, wherein the at least one neutralizing agent is selected from organic amines, alkali metal hydroxides, alkali earth metal hydroxides, alkali metal carbonates, alkali metal phosphates, and mixtures thereof;
   (c) 0.1% to 20% by weight at least of at least one thickening agent selected from celluloses and their derivatives, nonionic guar gums, scleroglucan gum, xanthan gum, carrageenan, pectins, starches, and mixtures thereof;

(d) 1% to 80% by weight of at least one fatty substance selected from alkanes, esters of fatty acid, esters of fatty alcohol, hydrocarbons, silicones, non-silicone waxes, mineral oil, vegetable oils, non-silicone synthetic oils, fatty alcohols and mixtures thereof;

(e) 0.1% to 20% by weight of at least one nonionic surfactant selected from alkoxylated fatty alcohols, alkyl(ether)phosphates, alkylpolyglucosides, and mixtures thereof;

(f) 0.5% to 5% by weight of at least one quaternary ammonium compound; and (g) water;

wherein all weights are based on the total weight of the composition; and the composition is free of pyridine and derivatives thereof.

15. The composition of claim 14, wherein the pH of the composition ranges from 3 to 5.

16. The composition of claim 14, wherein the pH of the composition ranges from 2 to 4.

17. The composition of claim 14, wherein the at least one neutralizing agent is selected from organic amines.

18. The composition of claim 14, wherein the at least one fatty substance is selected from mineral oil, stearyl alcohol, cetearyl alcohol, cetyl alcohol, and mixtures thereof.

19. A process for shaping hair or altering the shape of hair or caring for the hair, the process comprising the steps of:

(1) applying onto hair, a composition according to claim 1;

(2) optionally, brushing or combing or smoothing the hair;

(3) heating the hair to a temperature of at least 40° C.; while optionally applying a smoothing action on the hair; and (4) optionally, rinsing the hair with water.

20. The process according to claim 19, further comprising the step of contacting the hair with a neutralizing composition comprising an oxidizing agent.

21. The process according to claim 19, further comprising the step of contacting the hair after step (3) with an intermediate agent selected from a shampoo, a conditioner, or both a shampoo and a conditioner, followed by rinsing with water.

* * * * *